US010744141B2

(12) United States Patent
Goutham et al.

(10) Patent No.: US 10,744,141 B2
(45) Date of Patent: *Aug. 18, 2020

(54) COMPOSITIONS AND METHODS FOR TREATING CANCER

(71) Applicants: CASE WESTERN RESERVE UNIVERSITY, Cleveland, OH (US); ICAHN SCHOOL OF MEDICINE AT MOUNT SINAI, New York, NY (US)

(72) Inventors: Narla Goutham, Pepper Pike, OH (US); Michael Ohlmeyer, New York, NY (US); Daniel McQuaid, Cleveland, OH (US)

(73) Assignees: CASE WESTERN RESERVE UNIVERSITY, Cleveland, OH (US); ICHAN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/738,870

(22) PCT Filed: Jun. 23, 2016

(86) PCT No.: PCT/US2016/039022
§ 371 (c)(1),
(2) Date: Dec. 21, 2017

(87) PCT Pub. No.: WO2016/210134
PCT Pub. Date: Dec. 29, 2016

(65) Prior Publication Data
US 2018/0185382 A1    Jul. 5, 2018

Related U.S. Application Data

(60) Provisional application No. 62/183,517, filed on Jun. 23, 2015.

(51) Int. Cl.
| | |
|---|---|
| *A61K 31/55* | (2006.01) |
| *A61K 45/06* | (2006.01) |
| *A61K 31/4375* | (2006.01) |
| *A61K 31/416* | (2006.01) |
| *A61P 35/00* | (2006.01) |
| *A61K 31/506* | (2006.01) |

(52) U.S. Cl.
CPC ............ *A61K 31/55* (2013.01); *A61K 31/416* (2013.01); *A61K 31/4375* (2013.01); *A61K 31/506* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 8,461,362 B2 * | 6/2013 | Chen | .................... C07D 311/72 549/407 |
| 9,134,297 B2 | 9/2015 | Narla et al. | |
| 9,254,299 B2 | 2/2016 | Hart et al. | |
| 2003/0045515 A1 | 3/2003 | Binderup et al. | |
| 2011/0033461 A1 | 2/2011 | Ratushny et al. | |
| 2012/0207767 A1 | 8/2012 | Buck et al. | |

FOREIGN PATENT DOCUMENTS

| | | | | |
|---|---|---|---|---|
| WO | 2009/117769 A1 | 10/2009 | | |
| WO | WO 2009/11769 | * | 10/2009 | ........... A61K 31/137 |
| WO | 2013/025882 A2 | 2/2013 | | |
| WO | 2014/151955 A1 | 9/2014 | | |
| WO | 2015/138500 A1 | 9/2015 | | |
| WO | 138496 A1 | 9/2015 | | |

OTHER PUBLICATIONS

Yu et al (Cancer Res 15:7421-7428, 2009) (Year: 2009).*
Yan, Ling, et al., "PP2A Regulates the Pro-apoptotic Activity of FOXO1", The Journal of Biological Chemistry, vol. 283, No. 12, pp. 7411-7420, Mar. 21, 2008.
Spinnler, Katrin, et al., "Role of Glycogen Synthase Kinase 3 (GSK-3) in innate immune response of human immature dendritic cells to Aspergillus fumigatus", Medical Mycology, Jun. 2010, 48, 589-597.
Kristen Keon Ciombor et al: Selumetinib for the treatment of cancer, Expert Opinion on Investigational Drugs, vol. 24. No. 1, Nov. 11, 2014 (Nov. 11, 2014). pp. 111-123.
Tanaka Y et al: "Protein Kinase C Promotes Apoptosis in LNCAP Prostate Cancer Cells Through Activation of P38 MAPK and Inhibition of the AKT Survival Pathway", Journal of Biological Chemistry, American Society for Biochemistry and Molecular Biology. US, vol. 278, No. 36, Sep. 5, 2003 (Sep. 5, 2003), pp. 33753-33762.
Partial European Search Report for Application No. EP 16815302, dated Feb. 8, 2019.
Wenwen Chien et al: "Activation of protein phosphatase 2A tumor suppressor as potential treatment of pancreatic cancer", Molecular Oncology, vol. 9, No. 4, Jan. 15, 2015 (Jan. 15, 2015), pp. 889-905.
A. Agarwal et al: "Antagonism of SET 1-13 Using OP449 Enhances the Efficacy of Tyrosine Kinase Inhibitors and Overcomes Drug Resistance in Myeloid Leukemia", Clinical Cancer Research, vol. 20, No. 8, Jan. 16, 2014 (Jan. 16, 2014), pp. 2092-2103.
Perrotti et al: "Protein phosphatase 2A: a target for anticancer therapy", Lancet Oncology, The, Jan. 1, 2013 (Jan. 1, 2013), pp. e229-e238.
Dorien Haesen et al: "The Basic Biology of PP2A in Hematologic Cells and Malignancies", Frontiers in Oncology, Frontiers Research Foundation, CH, vol. 4, Dec. 11, 2014 (Dec. 11, 2014), pp. 347-1.
Myeloid Neoplasia et al: "Regular Article 1-13 Antagonistic activities of the immunomodulator and PP2A-activating drug FTY720 (Fingolimod, Gilenya) in Jak2-driven hematologic malignancies", Sep. 12, 2013 (Sep. 12, 2013).

(Continued)

*Primary Examiner* — Craig D Ricci
(74) *Attorney, Agent, or Firm* — Tarolli, Sundheim, Covell & Tummino LLP

(57) ABSTRACT

A method of treating cancer in a subject in need thereof includes administering to the subject therapeutically effective amounts of a PP2A activator and a protein kinase inhibitor.

14 Claims, 9 Drawing Sheets

(56) References Cited

OTHER PUBLICATIONS

A. Khanna et al: "Cancerous Inhibitor of Protein Phosphatase 2A, an Emerging Human Oncoprotein and a Potential Cancer Therapy Target", Cancer Research, vol. 73, No. 22, Nov. 7, 2013 (Nov. 7, 2013), pp. 6548-6553.

Zhang Li et al: "FTY720 induces 1-3,6,1, autophagy-related apoptosis and hecroptosis in human glioblastoma cells", Toxicology Letters, vol. 236, No. 1, May 1, 2015 (May 1, 2015), pp. 43-59.

* cited by examiner

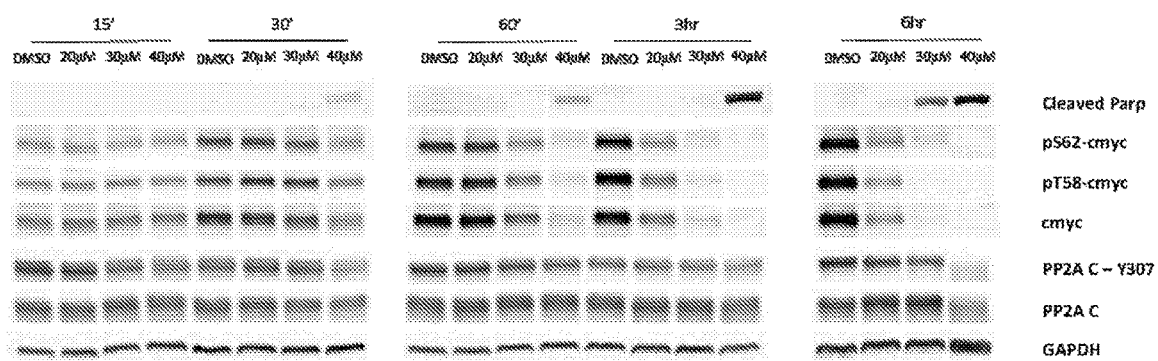
Fig. 3
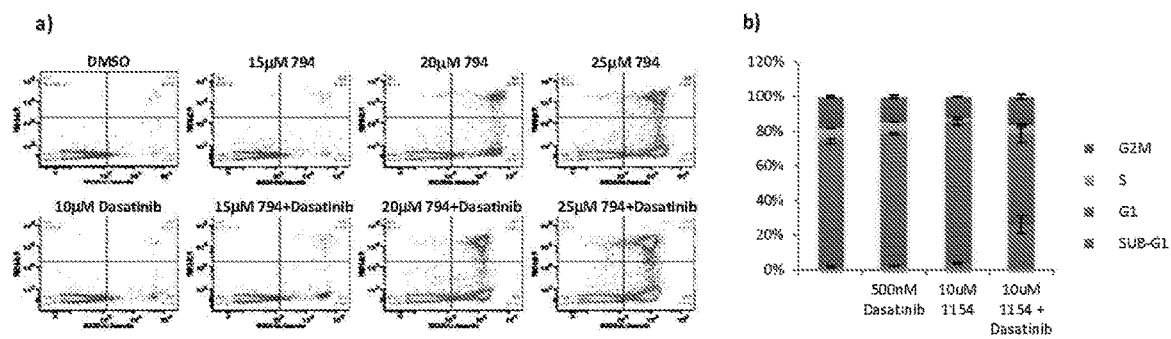
Figs. 4A-B

Figs. 4C-E

COMPOSITIONS AND METHODS FOR TREATING CANCER

RELATED APPLICATION

This application claims priority from U.S. Provisional Application No. 62/183,517, filed Jun. 23, 2015, the subject matter of which is incorporated herein by reference in its entirety.

BACKGROUND

Protein kinases have gained acceptance as therapeutic targets and have become a major focus of drug development efforts in oncology, with hundreds of inhibitors either in the pipeline or already in the clinic. Protein phosphatases, on the other hand, have been largely ignored for drug development because of their reputed lack of substrate specificity and the toxicity associated with natural products discovered as potent active site inhibitors.

Protein phosphatase 2A (PP2A) is one of the four major serine threonine phosphatases and is implicated in the negative control of cell growth and division. PP2A can dephosphorylate key oncogenic signaling proteins to function as a tumor suppressor. The PP2A protein phosphatase is a ubiquitous and conserved phosphatase with broad substrate specificity and diverse cellular functions. In contrast to the narrow substrate specificity of protein kinases, PP2A interacts with multiple substrates, and therefore its activation is, in effect, a combination therapy that coordinately inhibits multiple signaling pathways, including oncogenic signaling pathways. Among the targets of PP2A are proteins of oncogenic signaling cascades, such as Raf, MEK, AKT, ERK and FOXO.

SUMMARY

This application relates to compositions and methods for treating cancer and particularly relates to the use of PP2A activators and kinase inhibitors, and/or pharmaceutical compositions comprising the same, to treat cancer in subjects in need thereof.

In some embodiments, a method of treating cancer in a subject in need thereof can include administering to the subject therapeutically effective amounts of a PP2A activator and a protein kinase inhibitor. In some aspects, the subject can be a human subject. In other aspects, the cancer can be characterized by cancer cells in which PP2A expression is reduced. In still other aspects, the cancer can be selected from the group consisting of leukemia, prostate, endometrial and non-small cell lung cancer.

In some embodiments, the PP2A activator can include a small molecule that promotes and/or induces PP2A activation. For example, the PP2A activator can be triycyclic neuroleptic compound or a derivative thereof.

In some embodiments, the protein kinase inhibitor is selected from a MEK inhibitor, EGFR inhibitor, Her-2 kinase inhibitor, Src inhibitor, IKK inhibitor, Jak2 inhibitor, Aurora kinase inhibitor, CHK1 inhibitor, and a GSK-3 inhibitor.

In some embodiments, the amount of protein kinase inhibitor is subtherapeutic when administered in the absence of the PP2A activator. In other embodiments, the amount of PP2A activator is subtherapeutic when administered in combination with the protein kinase inhibitor.

In another embodiment, a method for treating cancer in a subject in need thereof includes administering to the subject a therapeutically effective amount of a pharmaceutical composition comprising a coformulation of a PP2A activator, a protein kinase inhibitor and a pharmaceutically acceptable carrier thereof.

BRIEF DESCRIPTION OF THE DRAWINGS

The foregoing and other features of the application will become apparent to those skilled in the art to which the application relates upon reading the following description with reference to the accompanying drawings, in which:

FIG. 3 illustrates a western blot analysis showing the kinetics of Y307 dephosphorylation and target engagement induced by Compound 1. Increasing doses of Compound 1 induce very rapid dephosphorylation of c-Myc, resulting in Parp cleavage in a similar time-dependent manner. However, Y307 dephosphorylation occurs as a secondary event to the initial PP2A activation, suggesting it is not necessary for Compound 1 to activate the phosphatase at very short timepoints.

DETAILED DESCRIPTION OF THE INVENTION

Figure 1:
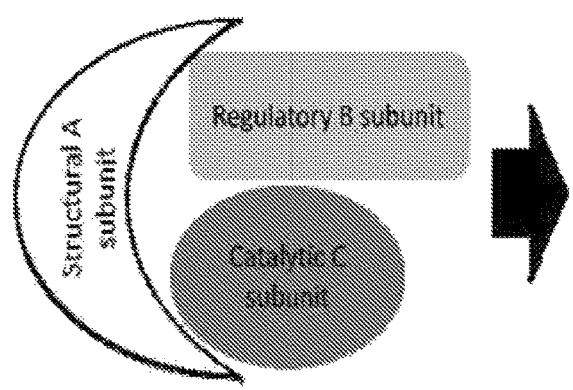
FIG. 1 is a schematic illustration showing that protein phosphatase 2A (PP2A) is composed of ABC subunits and dephosphorylates key oncogenic signaling proteins to function as a tumor suppressor.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the application.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the terms "treatment," "treating," or "treat" refer to any treatment of cancer, (e.g., leukemia, prostate cancer, and non-small-cell lung cancer) in a subject including, but not limited to, inhibiting disease development, arresting development of clinical symptoms associated with the disease, and/or relieving the symptoms associated with the disease. However, the terms "treating" and "ameliorating" are not necessarily meant to indicate a reversal or cessation of the disease process underlying the cancer afflicting the subject being treated. Such terms indicate that the deleterious signs and/or symptoms associated with the condition being treated are lessened or reduced, or the rate of progression or metastasis is reduced, compared to that which would occur in the absence of treatment. A change in a disease sign or symptom can be assessed at the level of the subject (e.g., the function or condition of the subject is assessed), or at a tissue or cellular level. In accordance with the present invention, desired mechanisms of treatment at the cellular level include, but are not limited to one or more of a reduction of cancer cell process extension and cell migration, apoptosis, cell cycle arrest, cellular differentiation, or DNA synthesis arrest.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those having an enhanced risk of developing precancers and cancers. An elevated risk represents an above-average risk that a subject will develop cancer, which can be determined, for example, through family history or the detection of genes causing a predisposition to developing cancer.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition is suitable for administration to a subject to achieve the treatments described herein, without unduly deleterious side effects in light of the severity of the disease and necessity of the treatment.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

As used herein, the term "effective amount" refers to an amount of a PP2A activator and an amount of a protein kinase inhibitor, the combination of which is sufficient to provide a desired effect. For example, a "therapeutically effective amount" provides an amount that is effective to reduce or arrest a disease or disorder such as abnormal cell growth or cell migration in a subject. The result can be a reduction and/or alleviation of the signs, symptoms, or causes of a disease or disorder, or any other desired alteration of a biological system. The effectiveness of treatment may be measured by evaluating a reduction in tumor load or tumor volume or decrease in tumor growth or tumor cell invasion and/or migration in a subject in response to the administration of a combination of a PP2A activator and a protein kinase inhibitor. The reduction in tumor load may be represent a direct decrease in mass, or it may be measured in terms of tumor growth delay, which is calculated by subtracting the average time for control tumors to grow over to a certain volume from the time required for treated tumors to grow to the same volume. The decrease in tumor cell metastasis may represent a direct decrease in tumor cell migration, or it may be measured in terms of the delay of tumor cell metastasis. An effective amount of a PP2A activator or protein kinase inhibitor in either case may be determined by one of ordinary skill in the art using routine experimentation.

The term "subject" for purposes of treatment includes any human or animal subject who has a disorder characterized by unwanted, rapid cell proliferation. Such disorders include, but are not limited to cancers and precancers. In particular embodiments, the subject includes any human or animal subject that is suspected of having or has been diagnosed with cancer. For methods of prevention the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

As used herein, the terms "subject diagnosed with cancer", "subject having cancer" or "subjects identified with cancer" refers to patient subjects that are identified as having or likely having cancer. Nonlimiting examples of diagnosing a subject with cancer include diagnoses using histological analysis conducted by a board-certified pathologist and diagnostic tests based on molecular approaches.

Embodiments described herein relate to compositions and methods for treating cancer, and particularly relates to the use of PP2A activators in combination with protein kinase inhibitors, and pharmaceutical compositions including the same, to treat cancer in subjects in need thereof. It has been shown that small molecule compounds can bind and activate protein phosphatase 2A (PP2A), a heterotrimeric tumor suppressor frequently inactivated in human cancer. However, the molecular mechanisms underlying this small molecule-based phosphatase activation had yet to be discovered. Using radiolytic mass spectrometry footprinting, the structural alterations of the PP2A complex were elucidated (see FIG. 2). Without being bound by theory, it is believed that PP2A activators protect amino acid residue Y307 from inhibitory phosphorylation as a mechanism to enzymatically activate this phosphatase and exert anticancer effects in cell culture and in vivo models without overt toxicity seen in other drugs through the subsequent downregulation of critical oncogenic signaling pathways, including c-Myc, Akt, MAPK, and ERK. These oncongenic signaling pathways can be leveraged to provide anti-cancer drug combinations of PP2A with protein kinase inhibitors, which can potentiate or synergistically enhance the anti-cancer effect of PP2A. In addition, it was discovered that at least some protein kinase inhibitors, such as SRC inhibitors, used in combination with PP2A activators can synergistically dephosphorylate Y307 and more avidly activate PP2A in multiple in vitro models of cancer. Accordingly, therapeutically effective amounts of PP2A activators can be administered in combination with protein kinase inhibitors to treat cancer in subjects in need thereof.

PP2A Activators

The PP2A activator can be any drug or compound, such as a pharmacologic chemical species, a complex (e.g., a metal complex), peptide agent, fusion protein, or oligonucleotide that activates the phosphatase and/or induces significant conformational changes in the PP2A complex resulting in decreased inhibitory phophorylation at the Y307 residue.

In some embodiments, PP2A activators can include small molecule activators of PP2A. For example, the PP2A activator can include tricyclic neuroleptic compound derivatives capable of inducing conformational changes in the PP2A complex resulting in decreased inhibitory phophorylation at Y307. In certain embodiments, the PP2A activator can include tricyclic neuroleptic compounds devoid of GPCR or monoamine transporter pharmacology.

In some embodiments, a small molecule tricyclic neuroleptic compound derivative PP2A activator for use in the present invention can include compounds of formula (I):

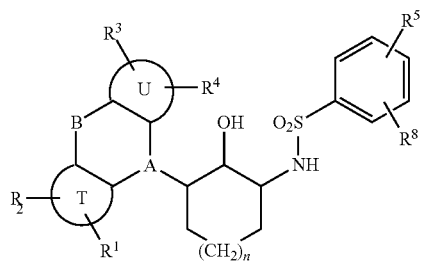

wherein:

B is selected from the group consisting of: direct bond, —O—, —(CH$_2$—O)—, —(O—CH$_2$)—, —C(=O)N(CH$_3$)— and —N(CH$_3$)C(=O)—;

A is selected from N and CH;

T is a benzene ring or a five or six membered heteroaromatic ring;

U is a benzene ring or a five or six membered heteroaromatic ring;

n is zero, 1 or 2;

$R^1$, $R^2$, $R^3$ and $R^4$ are chosen independently from H, OH, halogen, cyano, nitro, (C$_1$-C$_3$)alkylamino, (C$_1$-C$_3$)dialkylamino, (C$_1$-C$_3$)acylamino, (C$_1$-C$_3$)alkylsulfonyl, (C$_1$-C$_3$) alkylthio, (C$_1$-C$_3$)alkyl, (C$_1$-C$_3$)haloalkyl, (C$_1$-C$_3$)haloalkoxy, —CC(=O)O(C$_1$-C$_3$)alkyl, and (C$_1$-C$_3$)alkoxy; $R^5$ and $R^6$ are chosen independently from H, halogen, cyano, nitro, azido, (C$_1$-C$_3$)haloalkyl, (C$_1$-C$_3$)haloalkoxy, and (C$_1$-C$_3$)haloalkylthio.

C$_1$ to C$_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Loweracyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g., on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In preferred embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino, and benzyloxy.

In some embodiments, a small molecule PP2A activator can include compounds of formula (II):

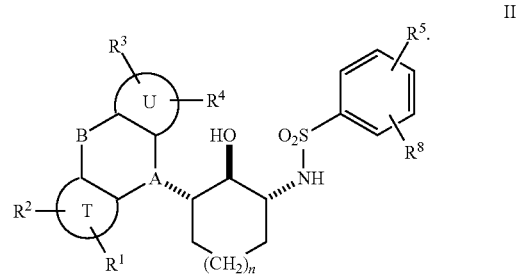

In some embodiments, a small molecule PP2A activator can include compounds of formula (IIIa) or IIIb:

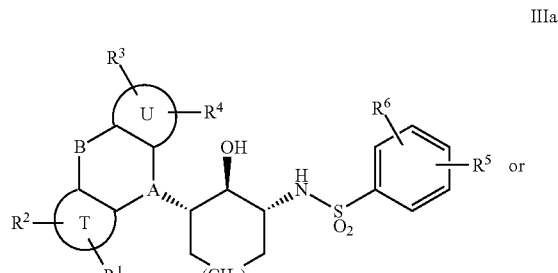

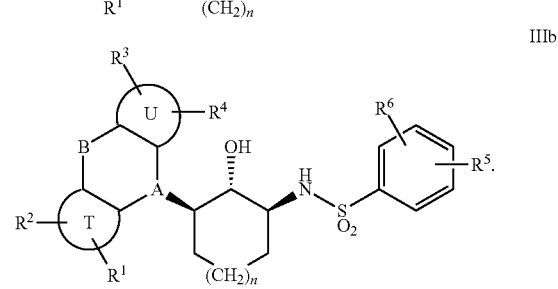

In the embodiments described below, the compound may be of formula I, II, IIIa or IIIb, unless otherwise indicated.

In some embodiments, n is one. These compounds may be envisioned as N-arylsulfonyl derivatives of 2-aminocyclohexanol:

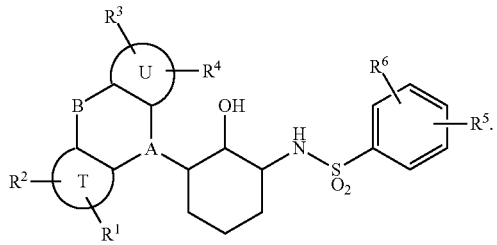

In some embodiments, n is zero. These compounds may be envisioned as N-arylsulfonyl derivatives of 2-aminocyclopentanol:

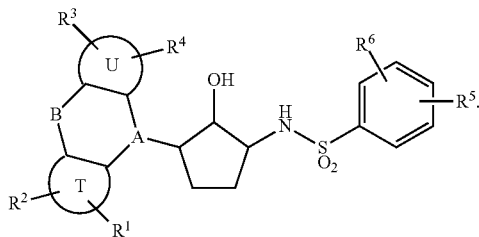

In some embodiments, n is two. These compounds may be envisioned as N-arylsulfonyl derivatives of 2-aminocycloheptanol:

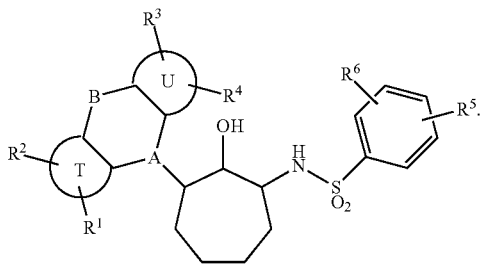

In any of the foregoing subgenera (cyclohexanol, cyclopentanol or cycloheptanol), preferred cycloalkanols are those in which the relative configurations are such that the amine and the tricycle are both trans to the alcohol:

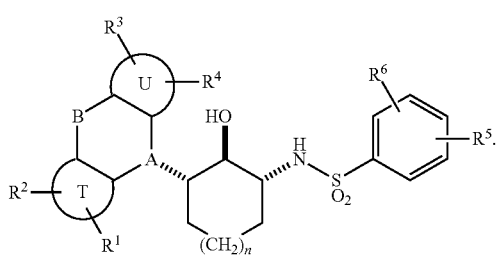

II

In this trans:trans subgroup, compounds can be either single enantiomers IIIa and IIIb or a mixture of the two. If a mixture, the mixture will most commonly be racemic, but it need not be. Substantially pure single enantiomers of biologically active compounds such as those described herein often exhibit advantages over their racemic mixture.

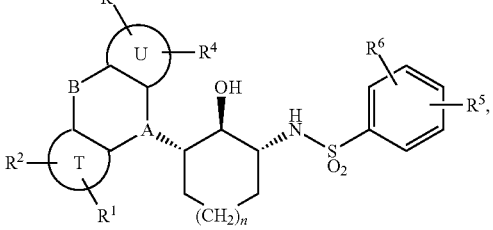

IIIa

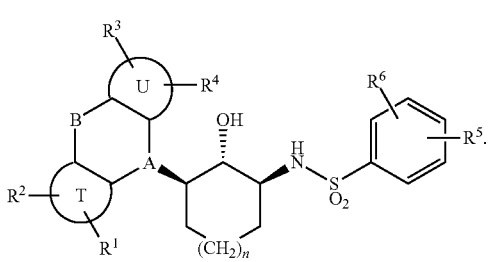

IIIb

In any of the foregoing subgenera (cyclohexanol, cyclopentanol or cycloheptanol), A may be N or CH. In both the N-series and the CH series, B may be a direct bond, —O—, —(CH$_2$—O)—, —(O—CH$_2$)—, —C(=O)N(CH$_3$)— or —N(CH$_3$)C(=O)—.

In some embodiments, at least one of T and U is a heterocycle such as pyridine, pyrimidine, diazine, thiophene, thiazole, oxazole, imidazole, pyrrole, or furan. In some embodiments, one of T and U is a benzene ring, and the other of T and U is selected from pyridine, pyrimidine, and thiophene. In other embodiments, T and U are both benzene rings.

When B is a direct bond, T and U are benzene rings and A is N, a subgenus of cycloalkanols in which the tricyclic substituent is a carbazole results:

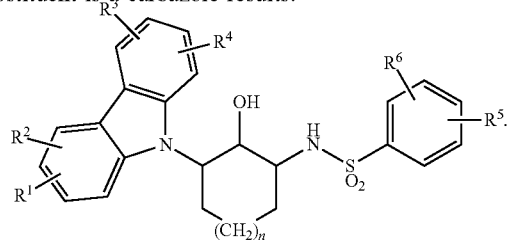

When B is —O—, T and U are benzene rings and A is N, a subgenus of cycloalkanols in which the tricycle is a dibenzooxazine results:

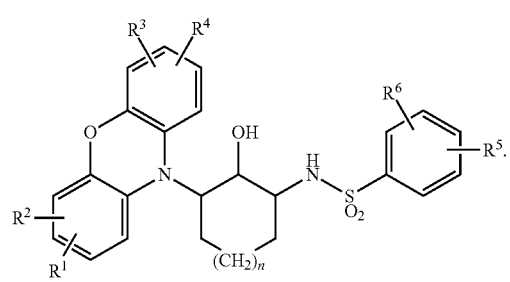

When B is —(CH₂—O)— or —(O—CH₂)—, T and U are benzene rings and A is N, two subgenera of cycloalkanols in which the tricyclic substituent is a dibenzooxazepine result:

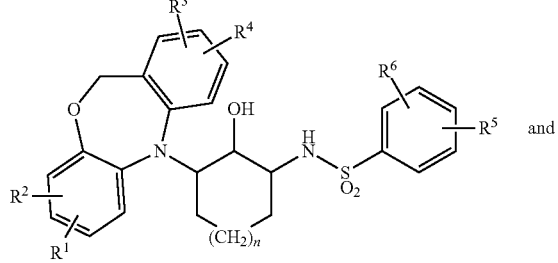

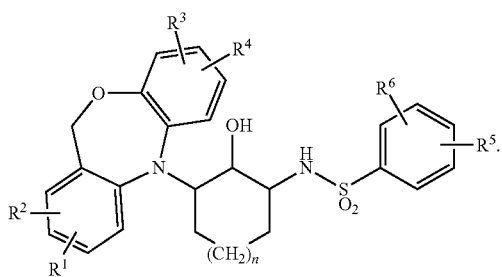

When B is —C(=O)N(CH₃)— or —N(CH₃)C(=O)—, T and U are benzene rings and A is N, two subgenera of cycloalkanols in which the tricyclic substituent is a dibenzodiazepine result:

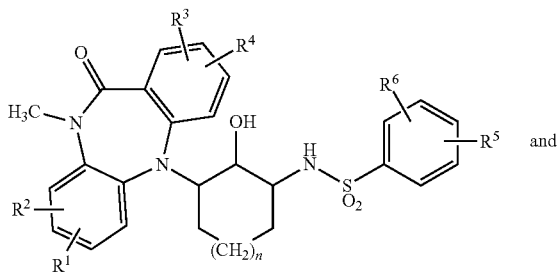

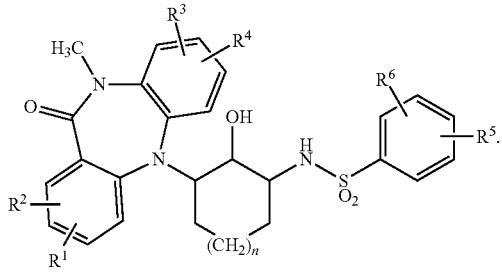

When B is a direct bond, T and U are benzene rings and A is CH, a subgenus of cycloalkanols in which the tricyclic substituent is a fluorene results:

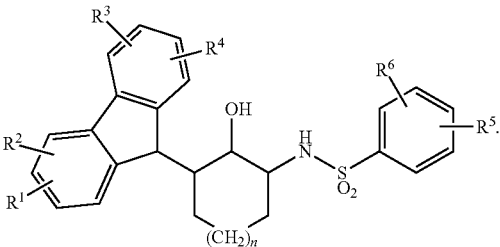

In some embodiments, $R^2$ and $R^4$ are H, and $R^1$ and $R^3$ are chosen independently from H, OH, F, Cl, Br, CN, $CO_2CH_3$, $CH_3$, $CF_3$, $OCF_3$, and $OCH_3$. In some embodiments, all of $R^1$, $R^2$, $R^3$ and $R^4$ are H. In some embodiments, at least one of $R^1$, $R^2$, $R^3$ and $R^4$ is located at a carbon two positions away from a bridgehead carbon. In some embodiments, $R^5$ is H, and $R^6$ is chosen from H, F, Cl, $CF_3$, $OCF_3$, $SCF_3$, $N_3$ and —CN. Often $R^6$ is in the para position.

Exemplary PP2A activators for use in the present invention can be selected from the group consisting of:

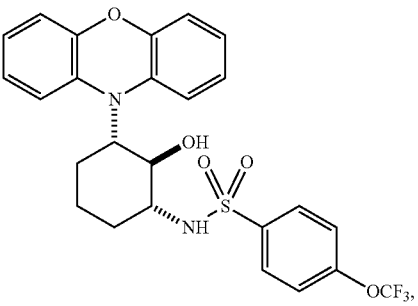

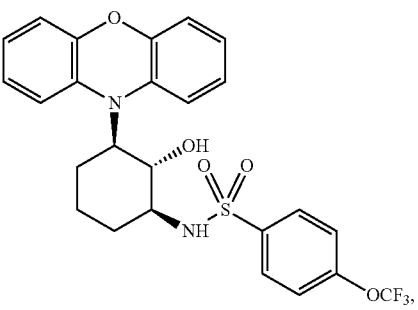

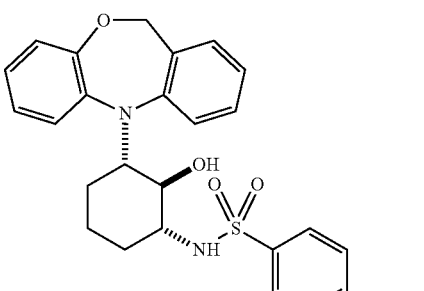

-continued
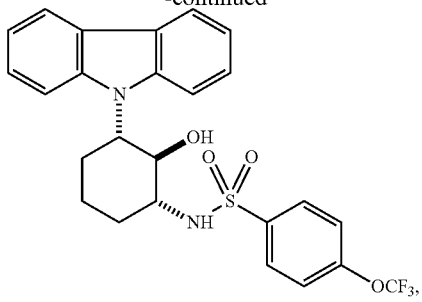
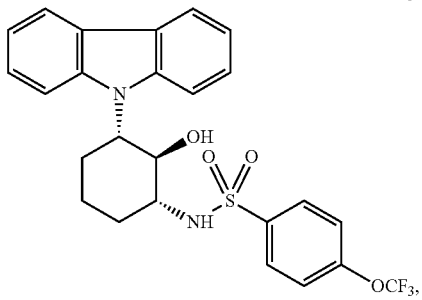
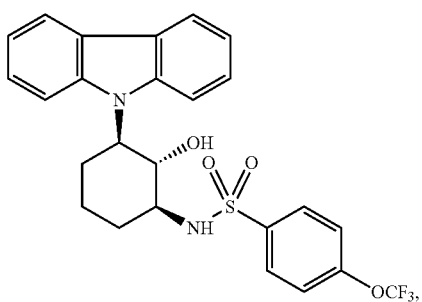
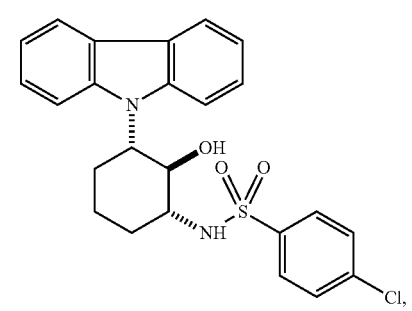
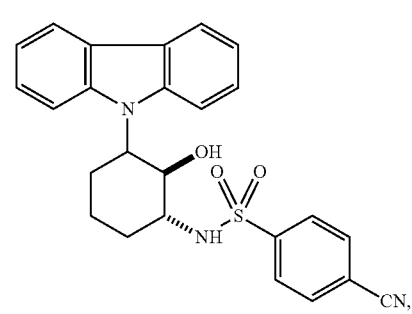
-continued
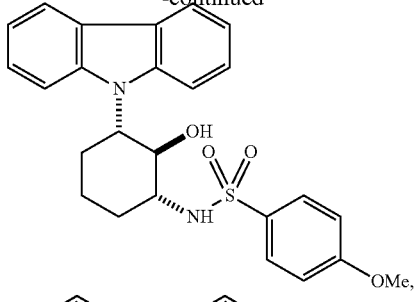
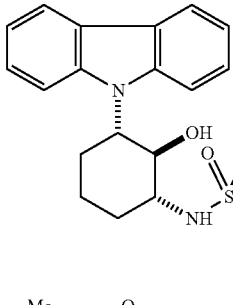
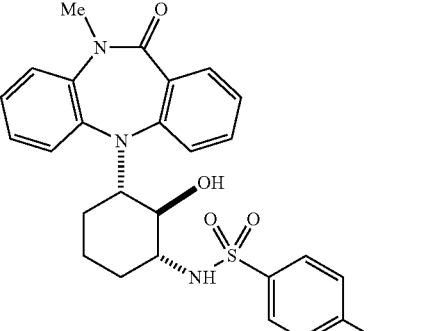
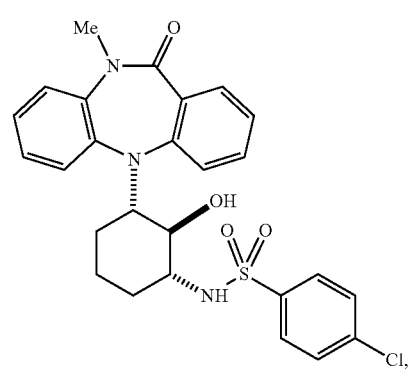
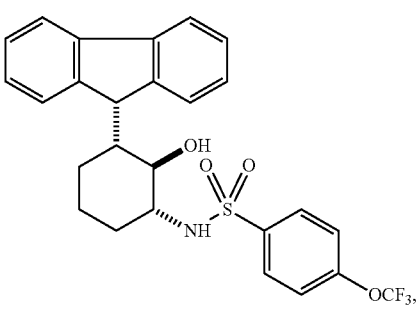

15
-continued
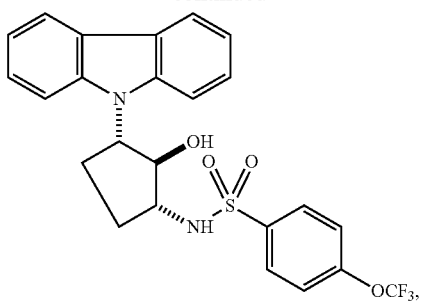
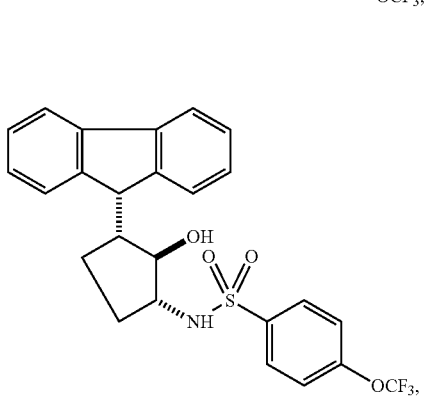
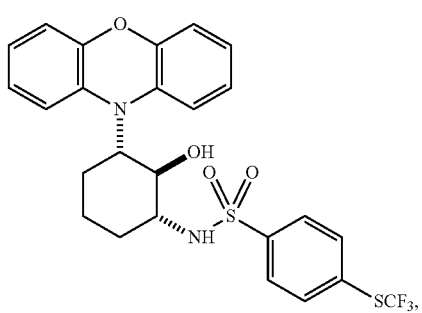
16
-continued
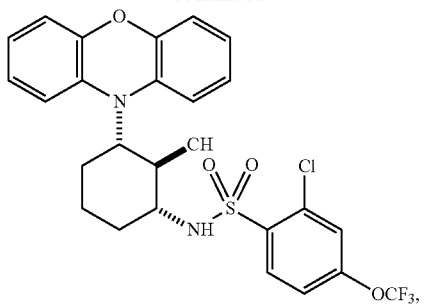
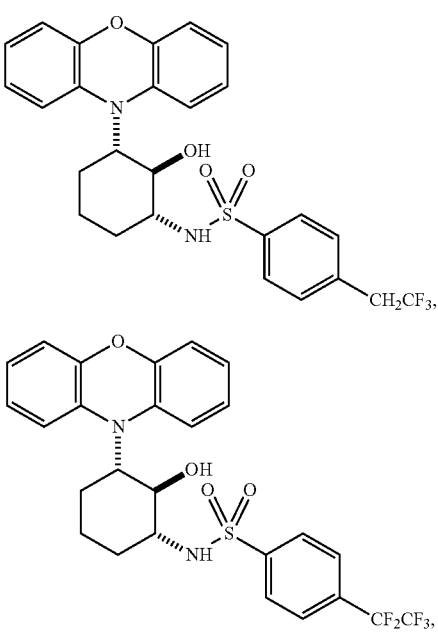
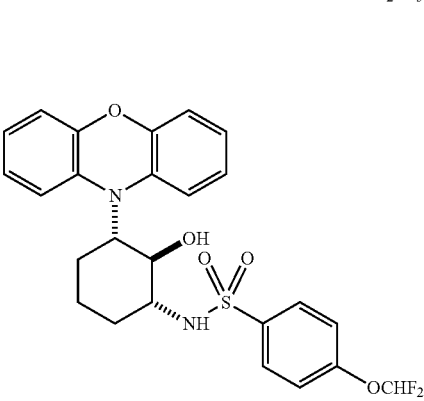
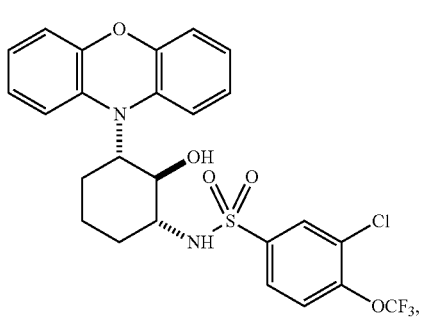

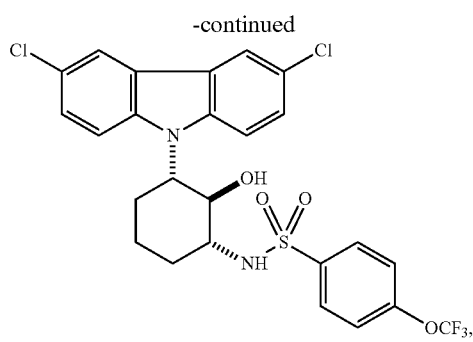
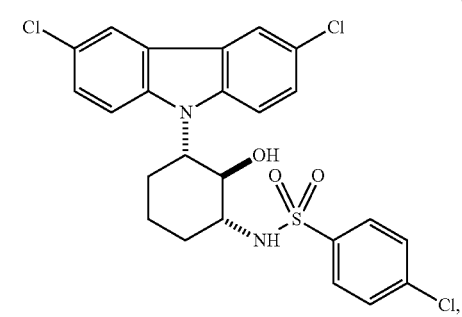
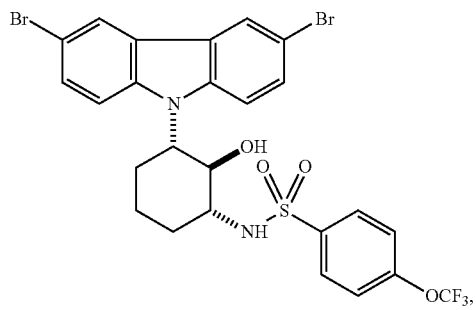
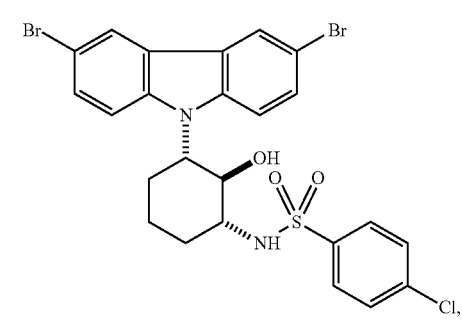
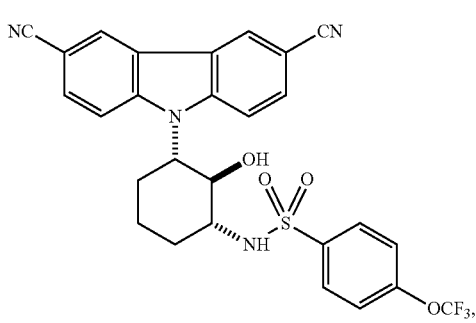
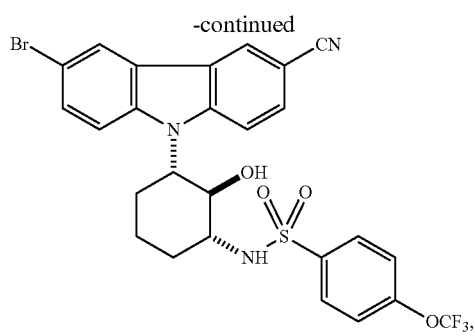
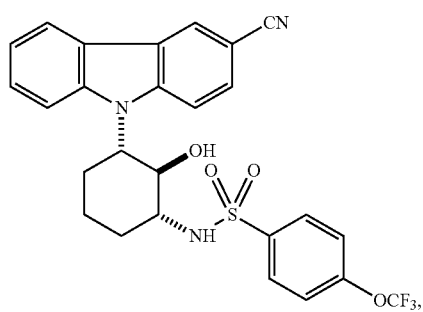
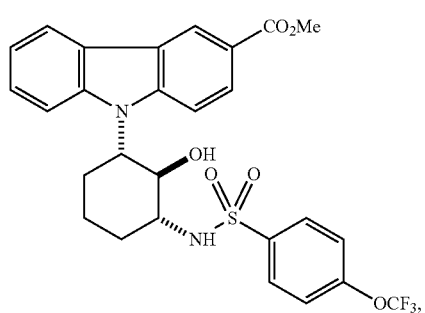
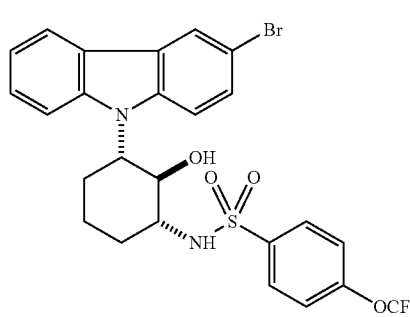
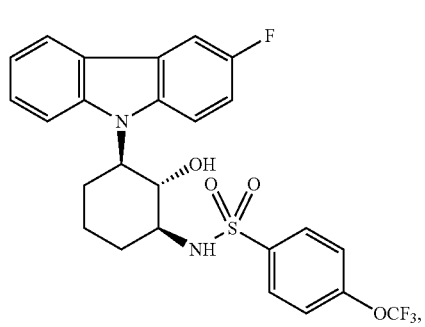

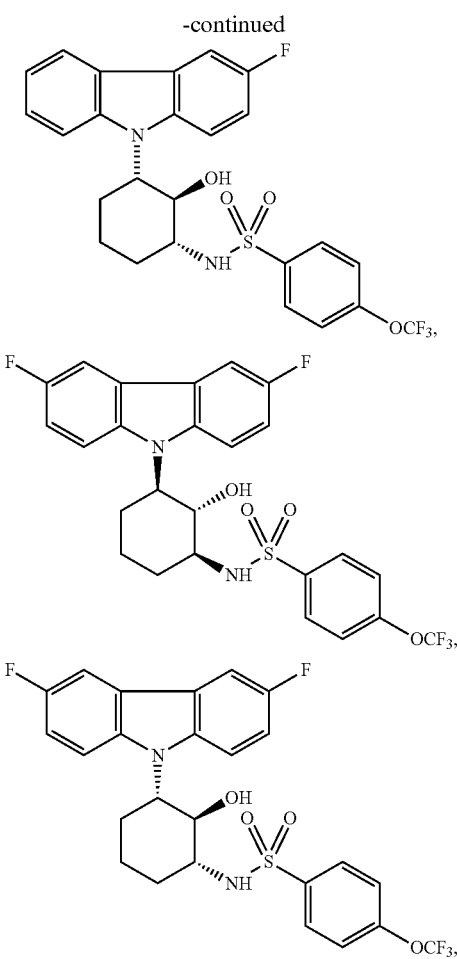
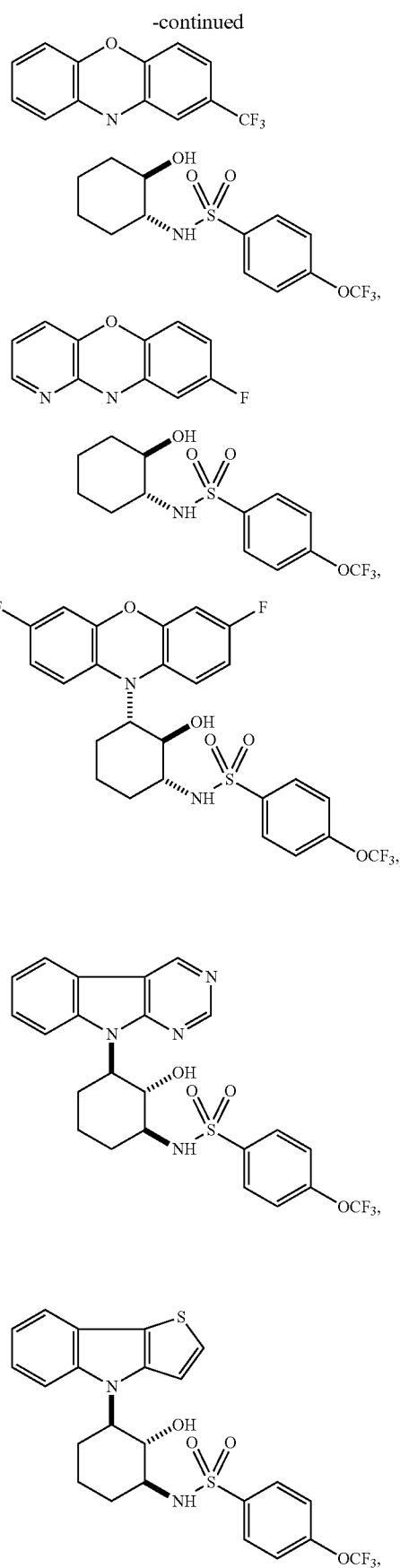

-continued

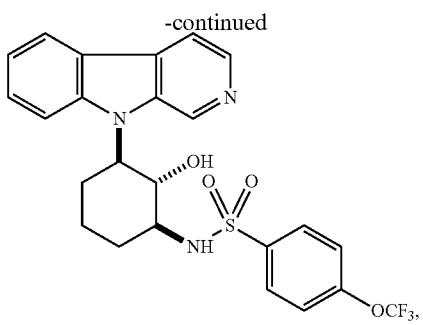

In some embodiments, a small molecule tricyclic neuroleptic compound derivative PP2A activator for use in the present invention can include compounds of formula (IV):

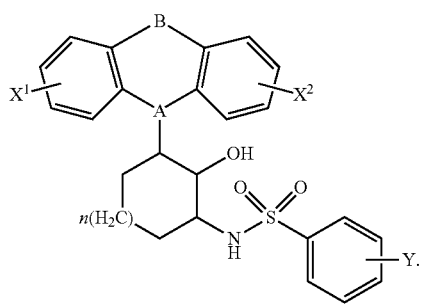

wherein:
B is selected from the group consisting of: —S—, —(CH$_2$—CH$_2$)—, and —CH=CH—;
A is selected from N and CH;
n is zero, 1 or 2;
$X^1$ is selected from —H, —F, —Cl, —CF$_3$, and —CN;
$X^2$ is selected from —H, —F, —Cl, —CF$_3$, and —CN; and
Y represents one or two substituents each independently selected from —H, —F, —Cl, —(C$_1$-C$_3$)haloalkyl, —(C$_1$-C$_3$)haloalkoxy, —(C$_1$-C$_3$)alkoxy, —C(=O)(C$_1$-C$_3$)alkyl, —C(=O)H, —(C$_1$-C$_3$)hydroxyalkyl, —(C$_1$-C$_3$)haloalkylthio, —N$_3$, and —CN.

In some embodiments, the invention relates to compounds of formula (V), wherein the relative configurations are such that the amine and the tricycle are both trans to the alcohol:

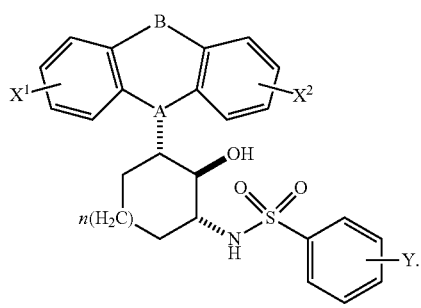

In this trans:trans subgroup, compounds can be either single enantiomers VIa and VIb or a mixture of the two. If a mixture, the mixture will most commonly be racemic, but it need not be. Substantially pure single enantiomers of biologically active compounds such as those described herein often exhibit advantages over their racemic mixture.

In some embodiments, the PP2A activator can include a compound of formula (VIa):

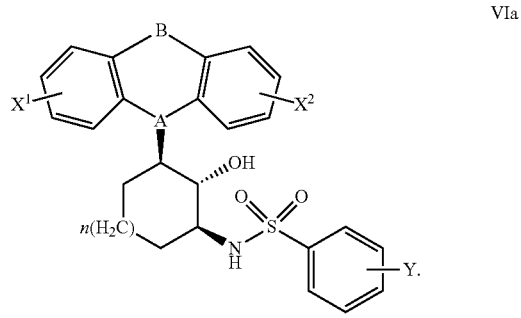

In some embodiments, the PP2A activator can include a compound of formula (VIb):

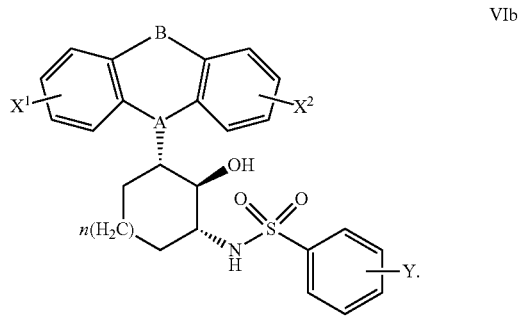

In the embodiments described below, the compound may be of formula IV, V, VIa or VIb, unless otherwise indicated.
In some embodiments, B is —(CH$_2$—CH$_2$)—. In some embodiments, B is —S—. In some embodiments, B is —CH=CH—.
In some embodiments, A is N. In some embodiments, A is CH.
In some embodiments, n is zero. In some embodiments, n is one. In some embodiments, n is two.
In some embodiments, $X^1$ is —H. In some embodiments, $X^1$ is —F. In some embodiments, $X^1$ is —Cl. In some embodiments, $X^1$ is —CF$_3$. In some embodiments, $X^1$ is —CN.
In some embodiments, $X^2$ is —H. In some embodiments, $X^2$ is —F. In some embodiments, $X^2$ is —Cl. In some embodiments, $X^2$ is —CF$_3$. In some embodiments, $X^2$ is —CN.
In some embodiments, $X^1$ and $X^2$ are both —H.
In some embodiments, Y is —H. In some embodiments, Y is —F. In some embodiments, Y is —Cl. In some embodiments, Y is —(C$_1$-C$_3$)haloalkyl. In some embodiments, Y is —CF$_3$. In some embodiments, Y is —CH$_2$CF$_3$ or —CF$_2$CF$_3$. In some embodiments, Y is —(C$_1$-C$_3$)haloalkoxy. In some embodiments, Y is —OCF$_3$. In some embodiments, Y is —OCHF$_2$. In some embodiments, Y is —(C$_1$-C$_3$)alkoxy. In some embodiments, Y is —OCH$_3$. In some embodiments, Y is —C(=O)(C$_1$-C$_3$)alkyl. In some embodiments, Y is —C(=O)CH$_3$. In some embodiments, Y is —C(=O)H. In some embodiments, Y is —(C$_1$-C$_3$)hydroxyalkyl. In some embodiments, Y is —C(CH$_3$)$_2$OH. In some embodiments, Y is —(C$_1$-C$_3$)haloalkylthio. In some embodiments, Y is —SCF$_3$. In some embodiments, Y is —N$_3$. In some embodiments, Y is —CN. In some embodiments, one instance of Y is H or Cl, and another instance of Y is selected from —H, —F, —Cl, —(C$_1$-C$_3$)haloalkyl, —(C$_1$-C$_3$)haloalkoxy, —(C$_1$-C$_3$)alkoxy, —C(=O)(C$_1$-C$_3$)alkyl, —C(=O)H, —(C$_1$-C$_3$)hydroxyalkyl, —(C$_1$-C$_3$)haloalkylthio, —N$_3$, and —CN. In some embodiments, one instance of Y is Cl, and another instance of Y is —OCF$_3$.

In some embodiments, B is —(CH$_2$—CH$_2$)— and n is one. One such example is shown below:

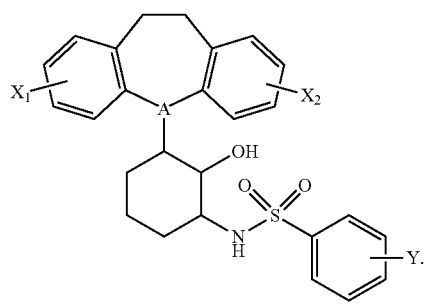

In some embodiments, B is —(CH$_2$—CH$_2$)—, A is N, and n is one. One such example is shown below:

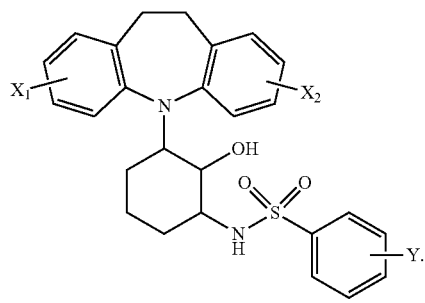

In some embodiments, B is —(CH$_2$—CH$_2$)— and A is N. One such example is shown below:

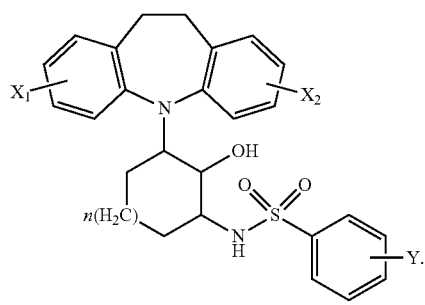

In some of these embodiments, X$^1$ and X$^2$ are both —H. In some embodiments, Y is in the para position, as shown below:

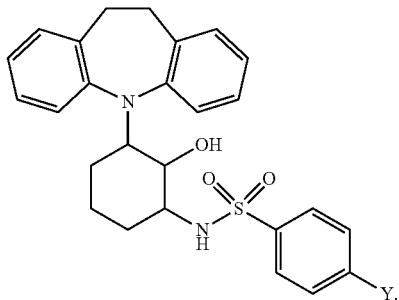

In some embodiments, Y is selected from —H, —F, —(C$_1$-C$_3$)haloalkyl, —(C$_1$-C$_3$)haloalkoxy, —(C$_1$-C$_3$)alkoxy, —C(=O)(C$_1$-C$_3$)alkyl, —C(=O)H, —(C$_1$-C$_3$)hydroxyalkyl, —(C$_1$-C$_3$)haloalkylthio, —N$_3$, and —CN. In some embodiments, Y is selected from —H, —F, —CF$_3$, —CH$_2$CF$_3$, —CF$_2$CF$_3$—OCF$_3$, —OCHF$_2$, —OCH$_3$, —C(=O)CH$_3$, —C(=O)H, —C(CH$_3$)$_2$OH, —SCF$_3$, —N$_3$, and —CN. In some embodiments, Y is —OCF$_3$.

The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. Unless otherwise stated, all tautomeric forms of the compounds of the invention are within the scope of the invention.

The compounds described herein contain one or more asymmetric centers and may thus give rise to enantiomers, diastereomers, and other stereoisomeric forms which may be defined in terms of absolute stereochemistry as (R)- or (S)—. The present invention is meant to include all such possible isomers. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; wavy lines indicate disavowal of any stereochemical implication which the bond it represents could generate; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representation

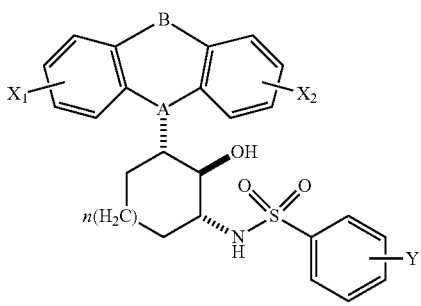

indicates either, or both, of the two trans:trans enantiomers:

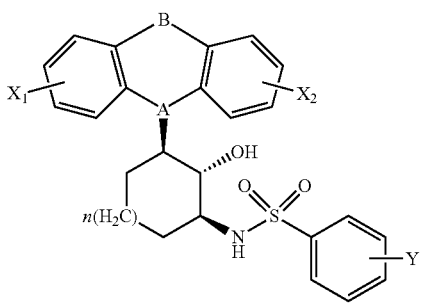

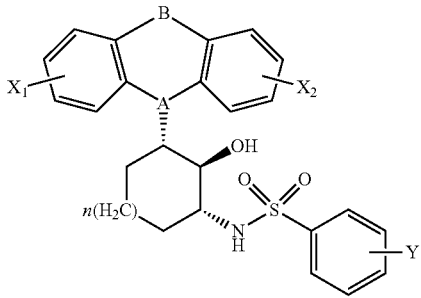

in any ratio, from pure enantiomers to racemates. The graphic representation:

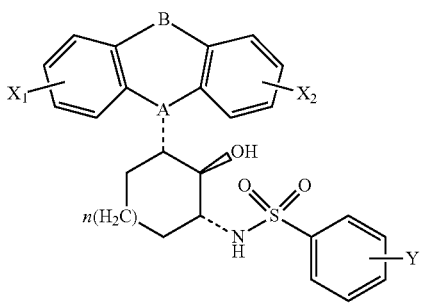

indicates a single enantiomer of unknown absolute stereochemistry, i.e., it could be either of the two preceding structures, as a substantially pure single enantiomer. And, finally, the representation:

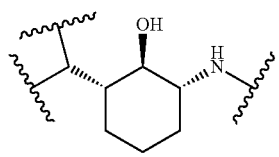 [SMILES: *N[C@@H]1CCC[C@H](C(*)*)[C@H]1O]

indicates a pure (1R,2R,6S)-2-amino-6-(C-attached tricycle) cyclohexanol. For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers. In the text describing the stereochemistry of the examples, the convention of Chemical Abstracts is used. Thus "(1R, 2R,6S)-rel-" indicates that the three chiral centers are in that relative relationship, which would be depicted in a structural diagram by solid bold and dashed lines, whereas "(1R,2R, 6S)" without the "rel" indicates a single enantiomer of that absolute configuration, which would be depicted in a structural diagram by solid and broken wedges.

In an exemplary embodiment, the PP2A activator can be selected from the group consisting of:

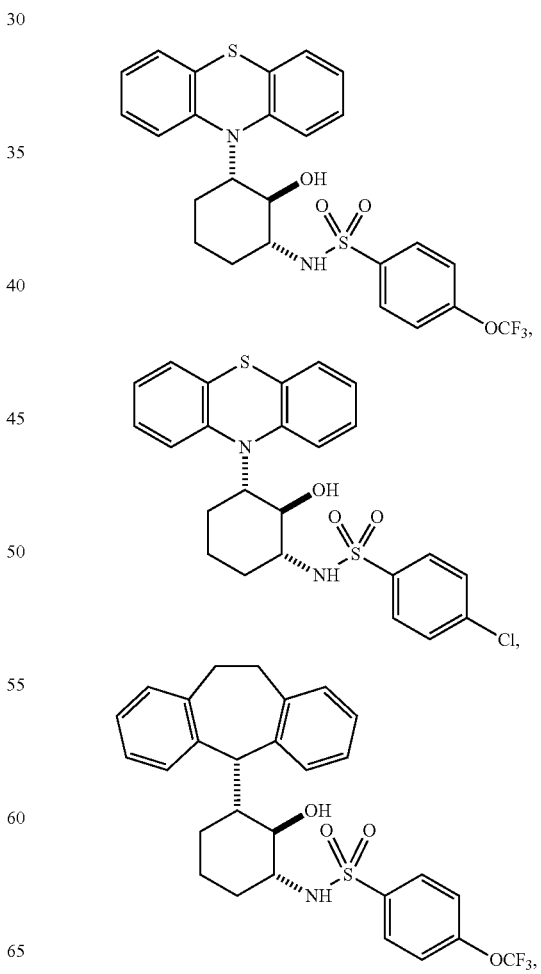

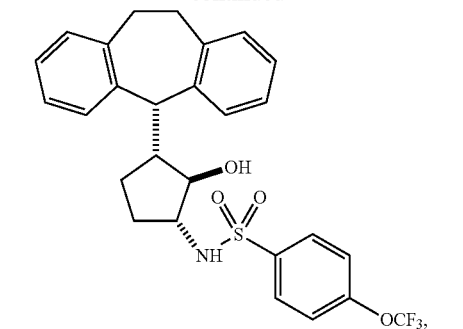
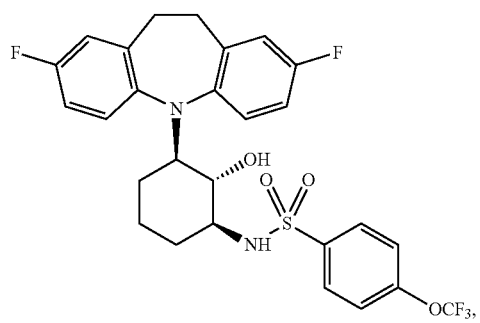
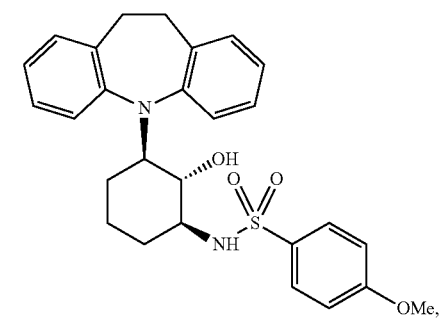
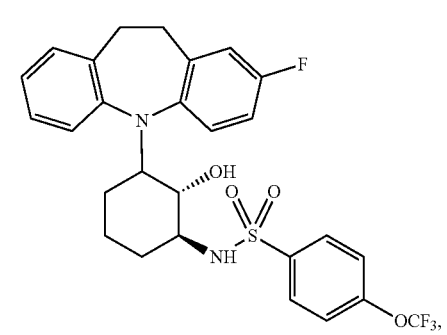
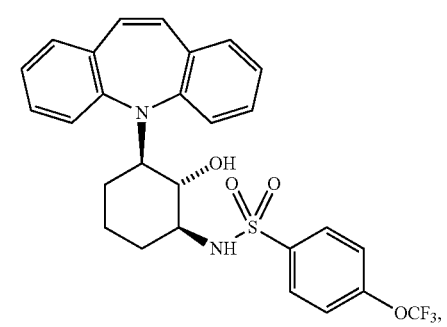
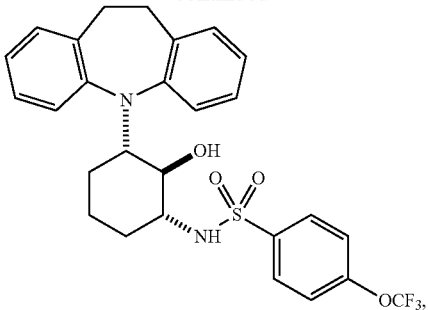
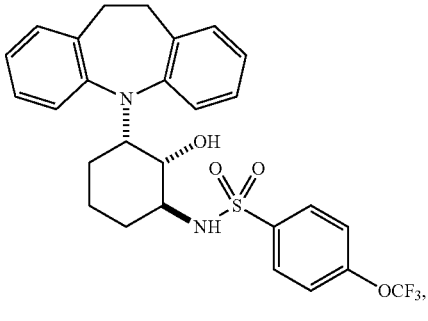
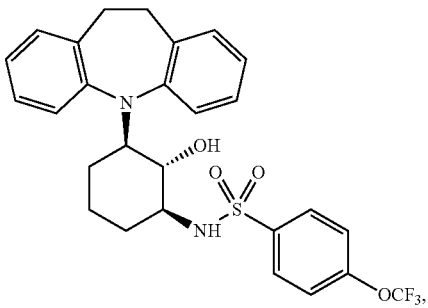
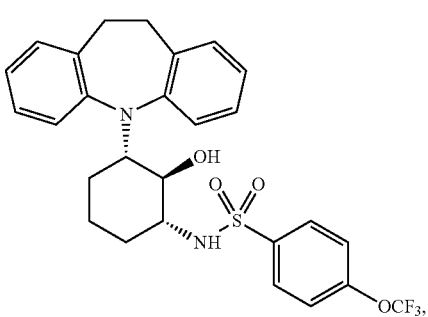
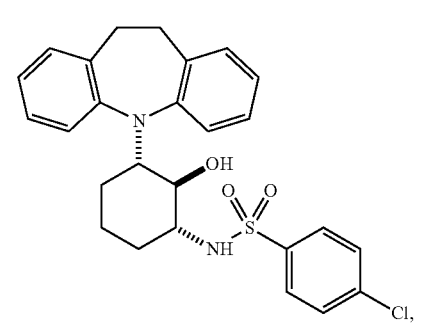

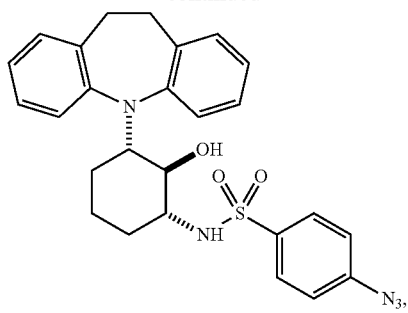
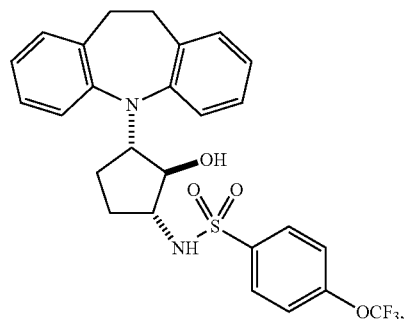
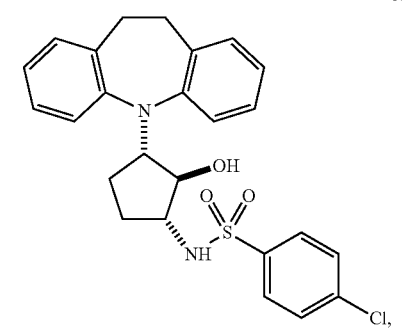
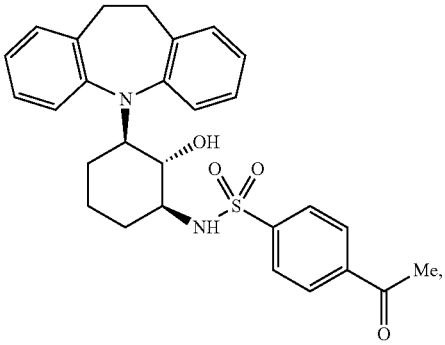
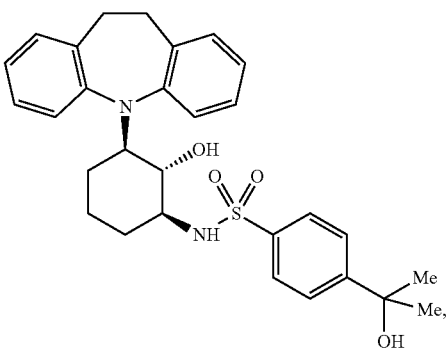
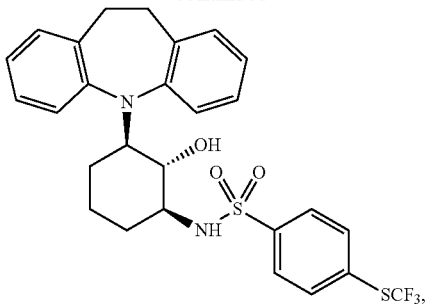
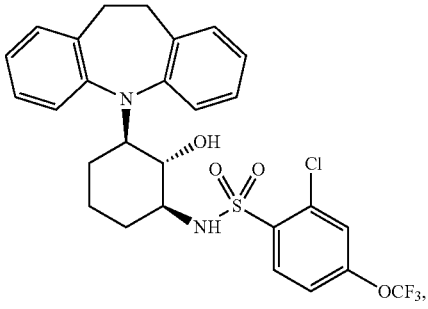
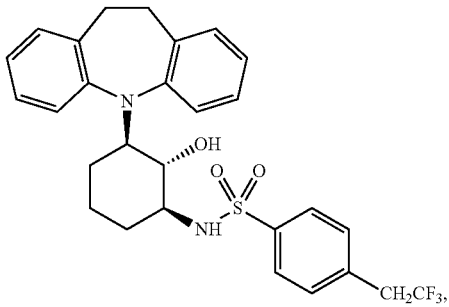
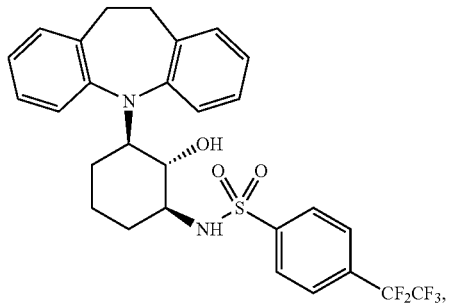
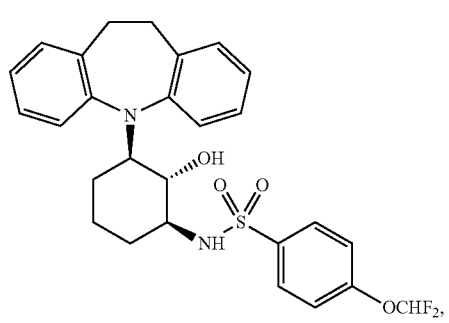

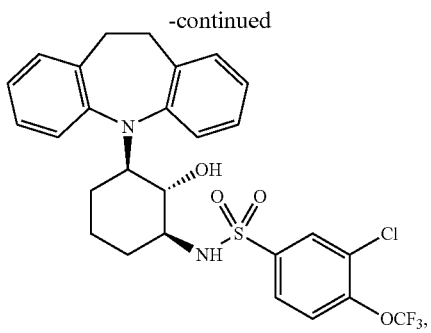

Additional agents capable of activating the PP2A phosphatase for use in methods described herein may be selected from the group consisting of, but not limited to, FTY720 (also called fingolimod), forskolin, 1,9-dideoxyforskolin, ceramides (also called sphingosines), such as C2-ceramide, topoisomerase inhibitors, such as etoposide (Eposin, Etopophos, Vepesid™, VP-16™), tubulin polymerisers, such as methyl-3,5-diiodo-4-(4'-methoxypropoxy)benzoate (DIME or DIPE), fatty acids, such as palmitate, and thiol alkylating agents such as N-ethylmaleimide (NEM).

Further agents for increasing PP2A activity for prophylaxis or treatment of cancers as described herein include genetic molecules, such as over expression constructs for the endogenous PP2A activator PTPA, PP2A or individual PP2A gene subunits. Similarly, such agents may also take the form of DNA/RNA inhibition molecules, such as shRNA or antisense sequences, including those specific to the endogenous PP2A inhibitor SET, or to an individual PP2A gene subunit or specific region of the PP2A gene (e.g., a transcriptional regulatory control subunit such as a promoter).

Candidate PP2A activators or activating agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al, Proc. Natl. Acad. Sci. USA, 92:3439-3443 (1995)). Candidate agents can be used in these animal models to determine if a candidate agent activates PP2A activity, decreases one or more of the symptoms associated with the cancer, including, for instance, cancer metastasis, cancer cell motility, cancer cell invasiveness, or combinations thereof.

Protein Kinase Inhibitors

Oncogene activation is characterized by the acquisition of mutations or amplifications of kinases, which phosphorylate proteins to induce specific growth and survival signaling pathways. Over activation of the mitogen-activated protein (MAP) kinase cascade is known to play an important role in cell proliferation and differentiation. This pathway can be activated when a growth factor binds to its receptor tyrosine kinase. This interaction promotes RAS association with RAF and initiates a phosphorylation cascade through MEK (MAP kinase) to ERK. The only known substrates for MEK phosphorylation are the MAP kinases, ERK1 and ERK2. Phosphorylation of MEK increases its affinity and catalytic activity toward ERK as well as its affinity for ATP. Constitutive activation of the MAPK pathway has been found in a number of diseases, for example, melanoma, pancreatic, colon, lung, kidney and ovarian cancers; in particular pancreatic, colon, lung, kidney and ovarian cancers.

Inhibition of these kinases represents a promising strategy for the treatment of some forms of cancer and many examples of kinase inhibitors have been described in the scientific literature, including several examples useful in the treatment of human disease (see for example J. Zhang et al., Targeting cancer with small molecule kinase inhibitors, in Nature Reviews Cancer, volume 9, 2009, 28-39). PP2A can negatively or positively regulate many of the same signaling pathways as the kinase inhibitors, thus coadministration of PP2A activators with protein kinase inhibitors can enhance the anticancer effect of either class of compounds additively and/or synergistically. In some embodiments as shown in Example 2, the effect of PP2A activation and selective kinase inhibition on signaling pathways, such as canonical MAPK signaling, can be determined to design specific PP2A activator and kinase inhibitor combinations.

Given the synergistic effect of the coadministration of PP2A activators with protein kinase inhibitors, PP2A activators and protein kinase inhibitors when administered in combination can be at amounts or doses to achieve a therapeutic effect that are substantially less (i.e., subtherapeutic dose or amount) than the amounts or doses that would be required to achieve a therapeutic effect if each compound was administered alone. Co-administration of the PP2A activator and/or protein kinase inhibitors to the subject can also mitigate resistance to one single agent. Such resistance results either in the requirement for higher dosages of the drug and/or the renewed symptoms. Therefore, there is a practical upper limit to the amount that a subject can receive. However, if two or more agents are used in concert, the dosage of any single drug can be lowered. This is beneficial to the patient since using lower levels of therapeutic agents is generally safer for the patient. Thus in some aspects of the present invention, the compositions described herein can be administered to a subject at a subtherapeutic level.

In some embodiments, the amount of protein kinase inhibitor is subtherapeutic when administered in the absence of the PP2A activator. In other embodiments, the amount of PP2A activator is subtherapeutic when administered in combination with the protein kinase inhibitor. In still other embodiments, the amounts of protein kinase inhibitor and PP2A activator administered are subtherapeutic when the protein kinase inhibitor and PP2A activator are administered alone.

In some embodiments, the kinase inhibitor administered in combination with a PP2A activator is an MEK inhibitor. The term MEK inhibitor refers to a compound or agent, such as a small molecule, that inhibits, decreases, lowers, or reduces the activity of mitogen activated protein kinase (MEK). Inhibiting MEK enzymatic activity in turn reduces the ability of MEK to phosphorylate a substrate peptide or protein. MEK1 and MEK2 are protein kinases that participate in the RAS-RAF-MEK-ERK signal transduction cascade. Accordingly, the term "MEK inhibitors" encompasses within its scope a compound that is capable of inhibiting MEK.

The addition of a MEK inhibitor in combination with a PP2A activator can lead to a significant inhibition of ERK signaling and consequently a decrease in cancer cell proliferation. Since MEK inhibitor treatments alone have led to dose limiting toxicities in the clinic, a PP2A activator and MEK inhibitor combination represents a superior treatment strategy.

Examples of MEK inhibitors are AS703026 (EMD Serono); MSC1936369B (EMD Serono); GSK1120212 (GlaxoSmithKline); AZD6244 (6-(4-Bromo-2-chloro-phenylamino)-7-fluoro-3-methyl-3H-benzoimida-zole-5-carboxylic acid (2-hydroxy-ethoxy)-amide; selumetinib; Structure IV) (Memorial Sloan-Kettering Cancer Center); ARRY-438162 (Array BioPharma); RDEA119 (Ardea Biosciences, Inc.); GDC0941 (Genentech); GDC0973 (Genentech); TAK-733 (Millennium Pharmaceuticals, Inc.); RO5126766 (Hoffmann-La Roche); and XL-518 (Exelixis) U0126 (1,4-diamino-2,3-dicyano-1,4-bis[2-aminophenylthio]butadiene; ARRY-142886; Structure V). Further non-limiting examples of MEK inhibitors include PD-0325901, AZD2171, GDC-0973/XL-518, PD98059, PD184352, GSK1120212, RDEA436, RDEA119/BAY869766, AS703026, BIX 02188, BIX 02189, CI-1040 (PD184352), PD0325901, and PD98059. These and other inhibitors of MEK, as well as non-limiting examples of their methods of manufacture, are described in U.S. Pat. Nos. 5,525,625; 6,251,943; 7,820,664; 6,809,106; 7,759,518; 7,485,643; 7,576,072; 7,923,456; 7,732,616; 7,271,178; 7,429,667; 6,649,640; 6,495,582; 7,001,905; US Patent Publication No. US2010/0331334, US2009/0143389, US2008/0280957, US2007/0049591, US2011/0118298, International Patent Application Publication No. WO98/43960, WO99/01421, WO99/01426, WO00/41505, WO00/42002, WO00/42003, WO00/41994, WO00/42022, WO00/42029, WO00/68201, WO01/68619, WO02/06213 and WO03/077914, the contents of which are herein incorporated by reference in their entireties.

In other embodiments, the kinase inhibitor administered in combination with a PP2A activator is an IKK inhibitor. IKKs and related kinases positively regulate NF-κB by phosphorylating its inactive cytoplasmic complex with IκB to release NF-κB which translocates to the cell nucleus where it is transcriptionally active. NF-κB is a transcription factor whose dysregulation and overactivation has been implicated in the pathogenesis of many cancers, for example malignant melanoma. (see for example D. Melisi and P. Chaio, NF-kB as a target for cancer therapy in Expert Opin. Ther. Targets (2007) 11(2):133-144 and Michael Karin et al., THE IKK NF-κB SYSTEM: A TREASURE TROVE FOR DRUG DEVELOPMENT, Nature Reviews Drug Discovery Volume 3 2004 17-26). PP2A negatively regulates NF-κB, for example by dephosphorylation of its Rel-A subunit, see J. Yang et al., Protein Phosphatase 2A Interacts with and Directly Dephosphorylates RelA, Vol. 276, No. 51, December 21, pp. 47828-47833, 2001 and X. Lu and W. Yarbrough, Negative regulation of RelA phosphorylation: Emerging players and their roles in cancer, Cytokine & Growth Factor Reviews 26 (2015) 7-13.

Several IKK inhibitors have been developed to suppress or inhibit NF-κB function, for example, N-(6-chloro-9H-pyrido[3,4-b]indol-8-yl)nicotinamide [PS-1145]; N$^1$-(1,8-dimethylimidazo[1,2-a]quinoxalin-4-yl)ethane-1,2-diamine [BMS-345541]; 1-((5-methoxy-2-(thiophen-2-yl)quinazolin-4-yl)amino)-3-methyl-1H-pyrrole-2,5-dione [SPC-839]; N-(6-chloro-7-methoxy-9H-pyrido[3,4-b]indol-8-yl)-2-methylnicotinamide [ML120B]; 4-amino-[2,3'-bithiophene]-5-carboxamide [SC-514]; (E)-1-(6-(4-chlorophenoxy)hexyl)-2-cyano-3-(pyridin-4-yl)guanidine [CHS828 (GMX1778)]; and (Z)-3-(2,4-dimethyl-5-((2-oxoindolin-3-ylidene)ethyl)-1H-pyrrol-3-yl)propanoic acid [SU6668] as anticancer agents, see D. Lee and M. Hung, Advances in Targeting IKK and IKK-Related Kinases for Cancer Therapy, in Clin Cancer Res 2008; 14(18) Sep. 15, 2008. Coadministration of PP2A activating compounds with IKK inhibitors can therefore increase the effectiveness of either agent as an anticancer therapy.

Non-limiting examples of IKK kinase inhibitors include N-(6-chloro-9H-pyrido[3,4-b]indol-8-yl)nicotinamide; N$^1$-(1,8-dimethylimidazo[1,2-a]quinoxalin-4-yl)ethane-1,2-diamine; 1-((5-methoxy-2-(thiophen-2-yl)quinazolin-4-yl) amino)-3-methyl-1H-pyrrole-2,5-dione; N-(6-chloro-7-methoxy-9H-pyrido[3,4-b]indol-8-yl)-2-methylnicotinamide; 4-amino-[2,3'-bithiophene]-5-carboxamide; (E)-1-(6-(4-chlorophenoxy)hexyl)-2-cyano-3-(pyridin-4-yl)guanidine; and (Z)-3-(2,4-dimethyl-5-((2-oxoindolin-3-ylidene)methyl)-1H-pyrrol-3-yl)propanoic acid.

In other embodiment, the kinase inhibitor administered in combination with a PP2A activator is a Src or Jak2 kinase inhibitor. PP2A is subject to several levels of regulation including post translation modification by phosphorylation, for example see Maud Martin et al., Recent insights into Protein Phosphatase 2A structure and regulation: the reasons why PP2A is no longer considered as a lazy passive housekeeping enzyme in Biotechnol. Agron. Soc. Environ. 2010 14(1), 243-252 and V Jannsens et al. in PP2A holoenzyme assembly: in cauda venenum (the sting is in the tail) in Trends in Biochemical Sciences Vol. 33 (2008) No. 3, 113-121. Thus phosphorylation on tyrosine-307 of the catalytic subunit serves to inhibit or diminish phosphatase activity. Among the kinases known to phosphorylate tyrosine-307 of the PP2A catalytic subunit is Src (others are lck and Jak2), and several Src kinase inhibitors have been developed as anti-cancer agents in their own right, see for example L Kim et al, Src kinases as therapeutic targets for cancer, Nat. Rev. Clin. Oncol. 6, 587-595 (2009). Therefore, coadministration of PP2A activators described herein with a src or Jak2 kinase inhibitor will enhance the effectiveness of either agent as an anti-cancer therapy. In some embodiments, the protein kinase inhibitor is a src inhibitor. Non-limiting examples of Src kinase inhibitors include sarcatinib, dasatinib, bosutinib and KX01. In a specific embodiment, the Src kinase inhibitor is dasatinib.

In some embodiments, the protein kinase inhibitor is a Jak 2 inhibitor. Non-limiting examples of Jak 2 inhibitors include ruxolitinib, Baricitinib, CYT387, lestaurtinib, pacritinib and TG101348.

In some embodiments, the protein kinase inhibitor is an Aurora kinase inhibitor. Aurora kinase has been identified as a therapeutic target for cancer, see for example Katayama and Sen, Aurora kinase inhibitors as anticancer molecules, Biochimica et Biophysica Acta, 1799, 829-839 (2010). Aurora kinase family of serine/threonine kinases are important regulators of mitosis that are frequently over expressed in human cancers and have been implicated in oncogenic transformation including development of chromosomal instability in cancer cells. In addition, PP2A has been shown to negatively regulate Aurora kinases, see for example Horn et al., Functional Interaction of Aurora-A and PP2A during Mitosis, Mo. Biol of the Cell, 18, 1233-1241 (2007) and Sugiyama et al., Aurora-B associated protein phosphatases as negative regulators of kinase activation, Oncogene, 21, 3103-3111 (2002). Therefore, coadministration of PP2A activators described herein with an Aurora kinase inhibitor will enhance the effectiveness of either agent as an anti-cancer therapy. Aurora kinase inhibitors for use in a method described herein can include an Aurora A, B and/or C protein kinase inhibitor. Non-limiting examples of an Aurora kinase inhibitor include ZM447439, VX-680 (MK-0457), Hesperadin, PHA-680632, PHA-739358, Compound 677, JNJ-7706621, MLN8054, MLN8237, AZD1152, AS703569, PF-03814735, and SNS-314.

In still other embodiments, the protein kinase inhibitor can be a Chk1 kinase inhibitor. PP2A can interact with endogeneous inhibitor proteins, such as CIP2A. Decreased expression of inhibitor proteins, such as CIP2A, promotes PP2A activity. Chk1 kinase inhibitors have been reported as anticancer agents in their own right and furthermore Chk1 kinase inhibition has been shown to decrease CIP2A expression and promote PP2A activity, see A. Khanna et al, Chk1 Targeting Reactivates PP2A Tumor Suppressor Activity in Cancer Cells, Cancer Res; 73(22) Nov. 15, 2013. Thus, coadministration of PP2A activators described above can increase the effectiveness of Chk1 kinase inhibitors as an anticancer therapy.

Examples of Chk1 kinase inhibitors include (S)-5-(3-fluorophenyl)-N-(piperidin-3-yl)-3-ureidothiophene-2-carboxamide [AZD-7762]; (S)-1-(5-bromo-4-methyl-2-(morpholin-2-ylmethoxy)phenyl)-3-(5-methylpyrazin-2-yl)urea [LY2603618 (Rabusertib)]; 6-bromo-3-(1-methyl-1H-pyrazol-4-yl)-5-(piperidin-3-yl)pyrazolo[1,5-a]pyrimidin-7-amine [MK8776 (Sch900776)]; (S)-3-(1H-benzo[d]imidazol-2-yl)-6-chloro-4-(quinuclidin-3-ylamino)quinolin-2(1H)-one [CHIR-124]; and (R)-2-amino-2-cyclohexyl-N-(5-(1-methyl-1H-pyrazol-4-yl)-1-oxo-2,6-dihydro-1H-[1,2]diazepino[4,5,6-cd]indol-8-yl)acetamide [PF-477736].

In other embodiments, the protein kinase inhibitor can be a GSK-3 inhibitor. GSK-3 is a protein kinase whose dysregulation and over activation has been implicated in the pathology of several diseases including cancer (see for example: J. McCubrey et al. in "GSK-3 as potential target for therapeutic intervention in cancer", Oncotarget, volume 5, number 10, 2881-2911(2014); and A. Martinez et al. in "Glycogen Synthase Kinase 3 (GSK-3) Inhibitors as New Promising Drugs for Diabetes, Neurodegeneration, Cancer, and Inflammation" in Medicinal Research Reviews, Vol. 22, No. 4, 373-384, 2002). Several inhibitors of GSK3 and its isoforms have been developed and proposed as treatments for these conditions as reported in P. Cohen and M. Goedert, Nature Reviews Drug Discovery, volume 3, 479-487 (2004). 3-((3-chloro-4-hydroxyphenyl)amino)-4-(2-nitrophenyl)-1H-pyrrole-2,5-dione [SB415286]; 3-(2,4-dichlorophenyl)-4-(1-methyl-1H-indol-3-yl)-1H-pyrrole-2,5-dione [SB216763]; 6-((2-((4-(2,4-dichlorophenyl)-5-(4-methyl-1H-imidazol-2-yl)pyrimidin-2-yl)amino)ethyl)amino)nicotinonitrile [CHIR-99021 (CT-99021)]; $N^2$-(2-((4-(2,4-dichlorophenyl)-5-(1H-imidazol-2-yl)pyrimidin-2-yl)amino)ethyl)-5-nitropyridine-2,6-diamine [CHIR-98014]; 1-(quinolin-4-yl)-3-(6-(trifluoromethyl)pyridin-2-yl)urea [A1070722 (AXON 1909)]; 4-benzyl-2-(naphthalen-1-yl)-1,2,4-thiadiazolidine-3,5-dione [Tideglusib (NP-12, NP031112)]; and 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione [LY2090313]. Furthermore, GSK-3b has been found to negatively regulate PP2A by indirectly promoting the inhibitory PP2A tyrosine-307 phosphorylation of its catalytic subunit. Thus, inhibition of GSK-3b decreases PP2A tyrosine-307 phosphorylation in vitro and in vivo and hence activates PP2A. See X. Yao et al. in "Glycogen synthase kinase-3β regulates Tyr 307 phosphorylation of protein phosphatase-2A via protein tyrosine phosphatase 1B but not Src", Biochem. J. (2011) 437, 335-344. Thus, coadministration of a PP2A activator with a GSK-3 inhibitor will increase the effectiveness of either compound in the treatment of cancer. In some embodiments, the GSK-3 inhibitor is 3-((3-chloro-4-hydroxyphenyl)amino)-4-(2-nitrophenyl)-1H-pyrrole-2,5-dione; 3-(2,4-dichlorophenyl)-4-(1-methyl-1H-indol-3-yl)-1H-pyrrole-2,5-dione; 6-((2-((4-(2,4-dichlorophenyl)-5-(4-methyl-1H-imidazol-2-yl)pyrimidin-2-yl)amino)ethyl)amino)nicotinonitrile; $N^2$-(2-((4-(2,4-dichlorophenyl)-5-(1H-imidazol-2-yl)pyrimidin-2-yl)amino)ethyl)-5-nitropyridine-2,6-diamine; 1-(quinolin-4-yl)-3-(6-(trifluoromethyl)pyridin-2-yl)urea; 4-benzyl-2-(naphthalen-1-yl)-1,2,4-thiadiazolidine-3,5-dione; and 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione.

In still other embodiments, the protein kinase inhibitor can be an EGFR inhibitor. Epidermal Growth Factor Receptor (EGFR) is a member of the type 1 subgroup of receptor tyrosine kinase family of growth factor receptors which play critical roles in cellular growth, differentiation and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor alpha (TGF alpha), amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation. A number of human malignancies are associated with aberrant or overexpression of EGFR and/or overexpression of its specific ligands. Gullick, Br. Med. Bull. (1991), 47:87-98; Modijtahedi & Dean, Int. J. Oncol. (1994), 4:277-96; Salomon, et al., Crit. Rev. Oncol. Hematol. (1995), 19:183-232. Aberrant or overexpression of EGFR has been associated with an adverse prognosis in a number of human cancers, including head and neck, breast, colon, prostate, lung (e.g., NSCLC, adenocarcinoma and squamous lung cancer), ovarian, gastrointestinal cancers (gastric, colon, pancreatic), renal cell cancer, bladder cancer, glioma, gynecological carcinomas and prostate cancer. In some instances, overexpression of tumor EGFR has been correlated with both chemoresistance and a poor prognosis. Lei, et al., Anti-cancer Res. (1999), 19:221-28; Veale, et al., Br. J. Cancer (1993); 68:162-65. Mutations in EGFR are associated with many types of cancer as well. For example, EGFR mutations are highly prevalent in non-mucinous BAC patients. Finberg, et al., J. Mol. Diagnostics. (2007) 9(3):320-26. In an embodiment, the EGFR inhibitor is an antibody, such as Erbitutux. (cetuximab, Imclone Systems Inc.) and ABX-EGF (panitumumab, Abgenix, Inc.). In another embodiment the EGFR inhibitor is a small molecule that competes with ATP, such as Tarceva (erlotinib, OSI Pharmaceuticals), Iressa (gefitinib, Astra-Zeneca), tyrphostins described by Dvir, et al., J Cell Biol., 113:857-865 (1991); tricyclic pyrimidine compounds disclosed in U.S. Pat. No. 5,679,683; compound 6-(2,6-dichlorophenyl)-2-(4-(2-diethylaininoethoxy)phenylamino)-8-methyl-8H-pyrido(2,3-d)pyrimidin-7-one (known as PD166285) disclosed in Panek, et al., Journal of Pharmacology and Experimental Therapeutics 283, 1433-1444 (1997).

Additional protein kinase inhibitors for use in the treatment of cancer in accordance with methods described can include the small molecules afatinib, apatinib, axitinib, cabozantinib, canertinib, certinib, crenolanib, foretinib, crizotinib, dabrafenib, everolimus, ibrutinib, imatinib, lenvatinib, linifanib, motosanib, nilotinib, nintedanib, palbociclib, pazopanib, ponatinib, radotinib, regorafenib, sirolimus, sorafenib, sunitinib, tofacitinib, temsirolimus, trametinib, vandetanib, vatalanib, vemurafenib, fostamatinib, mubritinib, SU6656, the monoclonal antibodies bevacizumab, cetuximab, panitumumab, ranibizumab, trastuzumab, and the RNA aptamer pegaptanib.

Methods of Treating Cancer

The PP2A activators and protein kinase inhibitors described herein can be used in methods of treating cancer in a subject. The methods can include administering to the subject therapeutically effective amounts of at least one PP2A activator in combination with at least one protein kinase inhibitor described above, or pharmaceutically acceptable salt forms thereof.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

In some embodiments, the cancer is characterized by dysregulation of the PI3K-AKT-FOXO signaling pathway, the MAPK signaling pathway, and/or KRAS signaling pathway. The cancer can be selected from the group consisting of: ovarian, pancreatic, renal cell, breast, prostate, lung, hepatocellular carcinoma, glioma, leukemia, lymphoma, colorectal cancers, and sarcomas.

More particularly, cancers that may be treated by the compounds, compositions and methods described herein include, but are not limited to, the following: cardiac cancers, including, for example sarcoma, e.g., angiosarcoma, fibrosarcoma, rhabdomyosarcoma, and liposarcoma; myxoma; rhabdomyoma; fibroma; lipoma and teratoma; lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma; gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma; genitourinary tract cancers, including, for example, cancers of the kidney, e.g., adenocarcinoma, Wilms tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma; liver cancers, including, for example, hepatoma, e.g., hepatocellular carcinoma; cholangiocarcinoma; hepatoblastoma; angiosarcoma; hepatocellular adenoma; and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma; gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma; hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenström's macroglobulinemia; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. In certain embodiments, the cancer can be selected from leukemia, prostate, endometrial and non-small cell lung cancer.

Subjects potentially benefiting from the methods described herein include male and female mammalian subjects, including humans, non-human primates, and non-primate mammals. Other mammalian subjects include domesticated farm animals (e.g., cow, horse, pig) or pets (e.g., dog, cat). In some embodiments, the subject can include any human or animal subject who has a disorder characterized by unwanted, rapid cell proliferation of brain cells. Such disorders include, but are not limited to cancers and precancers, such as those described above. For methods of prevention, the subject can include any human or animal subject, and preferably is a human subject who is at risk of obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on.

In certain embodiments, prior to treatment, the patients are selected for having a particular cancer, or for being at risk of a particular cancer. The presence of cancer can be determined by means well known to clinicians. Initial assessment of cancer is based on symptoms presented by the patient. In addition, there are follow-up diagnostic procedures, including, but not limited to PET scans, CAT scans, biopsies, and bio-marker assessments.

Administration and Formulation Therapeutic Agents

Also provided herein are pharmaceutical compositions for the treatment of cancer, comprising a PP2A activator, a protein kinase inhibitor or a combination of a PP2A activator and a protein kinase inhibitor, or a pharmaceutically acceptable salt form thereof, and a pharmaceutically acceptable carrier or diluent.

While it may be possible for therapeutic compounds described herein to be administered as the raw chemical, it is preferable to present them as a pharmaceutical composition. Pharmaceutical compositions described herein can include a PP2A activator and/or a protein kinase inhibitor, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association one or more therapeutic compounds described above or a pharmaceutically acceptable salt thereof ("active ingredient") with the carrier which constitutes one or more accessory ingredients. In general, the formulations are prepared by uniformly and intimately bringing into association one or more active ingredients with liquid carriers or finely divided solid carriers or both and then, if necessary, shaping the product into the desired formulation.

Thus, in certain embodiments, formulations are prepared by uniformly and intimately bringing into association a PP2A activator and a protein kinase inhibitor with liquid carriers or finely divided solid carriers or both and then, if necessary, shaping the product into the desired formulation, thereby resulting in a coformulation of a PP2A activator and a kinase inhibitor for use in a method described herein.

Formulations that can be used for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

In some embodiments, PP2A activators and protein kinase inhibitors described above can be administered to a subject systemically, (i.e., enteral or parenteral administration). Preparations suitable for oral administration are a solution prepared by dissolving an effective amount of an agent or a pharmaceutically acceptable salt thereof in a diluent such as water, physiological saline, or orange juice; capsules, sachets or tablets comprising an effective amount of one or more therapeutic agents in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required. In some embodiments, the PP2A activators and/or protein kinase inhibitors may be incorporated into sustained-release preparations and devices.

The dosage of the PP2A activators and/or protein kinase inhibitors administered to the subject can vary depending on the kind and activity of active ingredient(s), seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg. In certain embodiments, dosage can be about 10 mg/kg. The daily dosage can be administered, for example in regimens typical of 1-4 individual administration daily. Other preferred methods of administration include intraarticular administration of about 0.01 mg to about 100 mg per kg body weight. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

In another embodiment, the practice of the method in conjunction with additional therapies is contemplated. Additional therapies can include conventional chemotherapy, radiation therapy or surgery directed against solid tumors and for control of establishment of metastases. For example, the administration of therapeutically effective amounts of a combination of a PP2A activator and a protein kinase inhibitor described herein may be conducted before, during or after chemotherapy, radiation therapy or surgery.

The phrase "combination therapy" embraces the administration of a combination of a PP2A activator and a protein kinase inhibitor and/or additional further therapies as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents (i.e., a PP2A activator and a protein kinase inhibitor), in a substantially simultaneous manner Substantially simultaneous administration can be accomplished, for example, by administering to the subject a single capsule including a coformulation of a PP2A activator and a kinase inhibitor having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a third and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

Thus, there is further provided a method of treating cancer comprising administering an effective amount of a PP2A activator and a protein kinase inhibitor, or pharmaceutically acceptable salt forms thereof, to a subject, wherein a therapeutically effective amount of one or more additional cancer chemotherapeutic agents are administered to the patient. In some embodiments, administration of a PP2A activator and a protein kinase inhibitor or pharmaceutically acceptable salt forms thereof, can restore sensitivity to one or more chemotherapeutic agents in a patient wherein the patient has developed a resistance to the one or more chemotherapeutic agents.

For the purposes of additional cancer chemotherapeutic agent therapy, there are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Suitable agents which may be used in combination therapy will be recognized by those of skill in the art.

Exemplary chemotherapeutic agents can include alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsulfam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

In some embodiments, radioprotective agents known to those of skill in the art for radiotherapy may be administered in combination with a PP2A activator and protein kinase inhibitor for the treatment of cancer in a subject. Radiotherapy may include ionizing radiation, particularly gamma radiation irradiated by commonly used linear accelerators or radionuclides. The radiotherapy by radionuclides may be achieved externally or internally. Radiotherapy may include brachytherapy, radionuclide therapy, external beam radiation therapy, thermal therapy (cryoablation hyperthermia), radiosurgery, charged-particle radiotherapy, neutron radiotherapy and photodynamic therapy, and the like.

Radiotherapy can be implemented by using a linear accelerator to irradiate the affected part with X-rays or an electron beam. While the X-ray conditions will differ depending on how far the tumor has advanced and its size and the like, a normal dose will be 1.5 to 3 Gy, preferably around 2 Gy, 2 to 5 times a week, and preferably 4 or 5 times a week, over a period of 1 to 5 weeks, for a total dose of 20 to 70 Gy, preferably 40 to 70 Gy, and more preferably 50 to 60 Gy. While the electron beam conditions will also differ depending on how far the tumor has advanced and its size and the like, a normal dose will be 2 to 5 Gy, preferably around 4 Gy, 1 to 5 times a week, and preferably 2 or 3 times a week, over a period of 1 to 5 weeks, for a total dose of 30 to 70 Gy, and preferably 40 to 60 Gy.

Treatment described herein can also be combined with treatments such as hormonal therapy, proton therapy, cryosurgery, and high intensity focused ultrasound (HIFU), depending on the clinical scenario and desired outcome.

The present invention is illustrated by the following examples. It is to be understood that the particular examples, materials, amounts, and procedures are to be interpreted broadly in accordance with the scope and spirit of the invention as set forth herein.

EXAMPLES

Example 1

Protein phosphatase 2A (PP2A) is a heterotrimeric serine/threonine phosphatase whose loss-of function mediates cancer development and progression. PP2A exerts its tumor suppressive properties via dephosphorylation of several oncogenic proteins (FIG. 1) implicated in a wide array of malignancies, including leukemia, prostate cancer, and non-small-cell lung cancer. However, its phosphatase activity is frequently inhibited in a myriad of cancers via mutation, decreased expression of its subunits, and upregulation of endogenous PP2A inhibitors. While the mechanism behind the PP2A inactivation mediated by inhibitors such as the SET protein has not been well described, many oncogenic kinases, such as SRC, have been shown to inhibit PP2A heterotrimeric formation via phosphorylation of the catalytic subunit at Tyrosine 307 (Y307). Y307 is a major inhibitory phosphorylation site on the C terminal tail of the complex, and constitutively phosphorylated mutants of this site have been shown to significantly inhibit B subunit binding to the PP2A A-C dimer and consequently substrate dephosphorylation.

Conversely, phosphorylation-deficient mutants exhibit increased heterorimeric formation and phosphatase activation, suggesting decreased phosphorylation at this tyrosine site could be a potential target to activate PP2A and potentiate its tumor suppressive properties. Combined, these findings suggest identifying new ways to maximally activate PP2A by decreasing inhibitory phosphorylation at Y307 with pharmacologic approaches may serve as a novel mechanism to induce apoptosis in cancer cells in which PP2A is inactive.

We developed a first-in-class pharmaceutically tractable series of PP2A activators capable of preventing dephosphorylation of the major inhibitory site on the PP2A catalytic subunit. In this Example, we describe for the first time that PP2A can be increasingly activated by maximally dephosphorylating this Y307 residue with novel pharmacological combination therapies with an FDA-approved SRC inhibitor, resulting in biological synergism.

We believe that this approach has broad implications for the treatment of cancers in which PP2A is inactivated and can drive our promising series of small molecule activators to increased activity in the clinic.

We also developed a series of novel derivatives of the tricyclic neuroleptics that retain the antiproliferative properties of the parent drugs but are devoid of the unfavorable central nervous system pharmacology. These re-engineered tricyclic compounds of the TRC series (Compound 1 and Compound 2, below) have been studied as anti-cancer agents in cell lines and xenograft models, and like their parent compounds, they produce their biological effects through activation of PP2A. Thus, we have called our novel agents Small Molecule Activators of PP2A (SMAPs). These SMAPs have shown promise as a monotherapy in multiple in vivo models, but leveraging combinations based upon well-studied molecular mechanisms regulating PP2A can broaden clinical applicability and potentially drive increased anticancer activity out of the series. With the new combination identified in these studies, we believe we have demonstrated novel pharmacological approaches to maximally activate PP2A and potentiate its anticancer effects in a variety of cancer models.

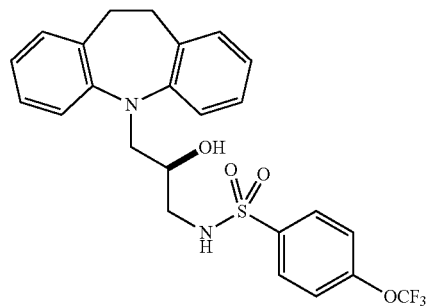

Compound 1

TRC-794

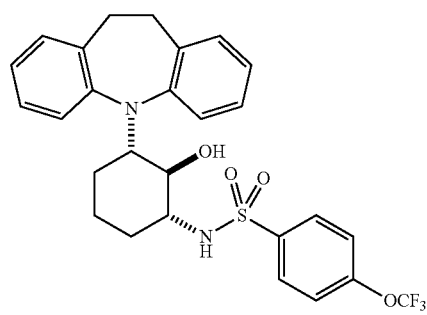

Compound 2

TRC-1154

Figure 2:
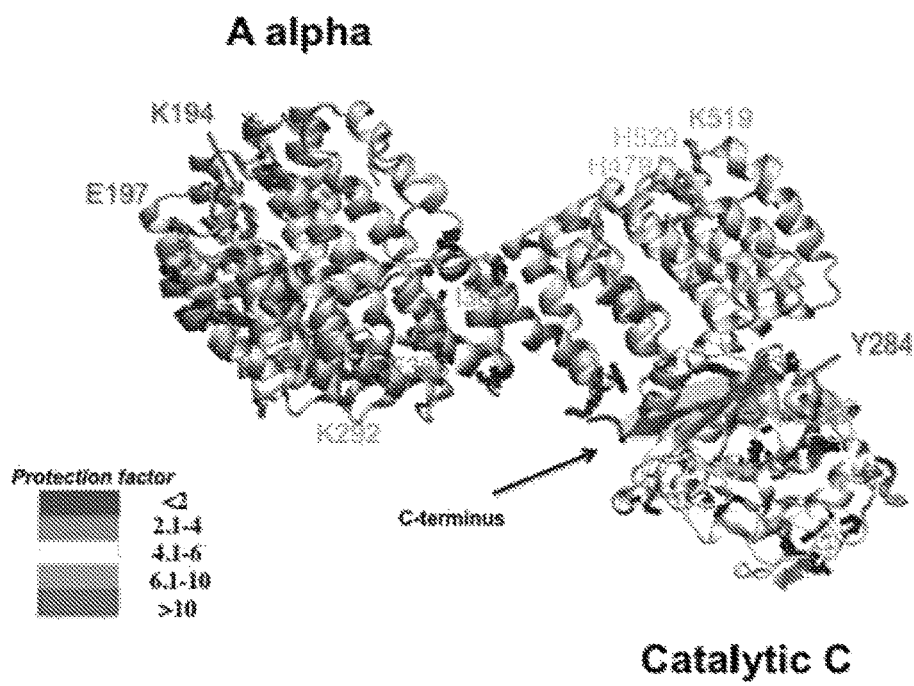
FIG. 2 is a model illustrating a visual representation of conformational changes in the PP2A A-C dimer as detected by radiolytic MS footprinting. Arrowed region indicates highly protected C-terminal tail of the catalytic subunit upon Example Compound 1 treatment.

Compound 1 Induces Significant Conformational Change in the PP2A A-C Dimer and Protects Y307 from Inhibitory Phosphorylation In order to elucidate the conformational changes in PP2A induced by SMAPs, we conducted structural mass spectrometry using radiolytic MS footprinting, a novel approach to probe the structural alterations of complexes such as PP2A. In these experiments, hydroxyl radicals are generated by an X-ray beam and oxidatively modify solvent-exposed amino acid side chains. Areas of a protein that are solvent inaccessible are spared these modifications and can be considered protected regions. Compared to the PP2A A-C dimer alone, addition of Compound 1 induced significant changes in solvent exposure in both the A and C subunits, indicating a conformational change (FIG. 2). Of note, the C terminal tail of the catalytic subunit displayed a 12-fold decrease in solvent accessibility in the presence of Compound 1 treatment compared to control (Table 1). The C terminal tail of the protein contains Y307, a major inhibitory phosphorylation site on PP2A that prevents heterotrimeric formation when phosphorylated, suggesting Compound 1 protects this site from inhibitory phosphorylation as a mechanism to enzymatically activate this phosphatase.

TABLE 1

Peptide sequences on the catalytic subunit with >4 fold protection factor upon Compound 1 treatment. The last row of peptide indicates the C-terminal tail, which is highly solvent exposed at baseline, but is 12-fold less exposed when Compound 1 is added to the dimer, indicating SMAP treatment protects this region of the C subunit as a potential means to mediate phosphatase activation.

| Peptide | Sequence | Residues Modified (SA) | Modification Rate, $S^{-1}$ No Ligand | Modification Rate, $S^{-1}$ + Ligand | Protection factor |
|---|---|---|---|---|---|
| [178-186]/C | DHIRALDRL | H179 | 17.2 ± 0.9 | 2.4 ± 0.2 | 7.2 |
| [198-217]/C | LLWSDPDDRGGWGISPRGAG | W200 | 11.1 ± 0.9 | 1.8 ± 0.2 | 6.2 |
| [200-217]/C | WSDPDDRGGWGIS PRGAG | W209 | 10.6 ± 0.6 | 2.3 ± 0.1 | 4.6 |
| [200-223]/C | WSDPDDRGGWGISPRGAGYTFGQD | W200 | 6.4 ± 0.3 | 1.4 ± 0.1 | 4.6 |
| | | W209 | 11.4 ± 0.6 | 2.1 ± 0.1 | 5.4 |
| | | Y218 | 0.28 ± 0.3 | 0.31 ± 0.03 | 0.9 |
| [259-265]/C | IFSAPNY | Y265 | 0.48 ± 0.04 | 0.12 ± 0.001 | 4.8 |
| [279-286]/C | DDTLKYSF | K283 | 2.1 ± 0.1 | 0.14 ± 0.01 | 15 |
| | | Y284 | 0.79 ± 0.1 | 0.13 ± 0.01 | 6.1 |
| [303-309]/C | RTPDYFL | Y or F | 6.9 ± 0.4 | 0.56 ± 0.06 | 12.0 |

Compound 1 Mediated Y307 Dephosphorylation does not Precede Target Engagement and In Vitro Activity To evaluate the kinetics of Y307 dephosphorylation in the context of SMAP-mediated phosphatase activation, a time course study was conducted in the c-Myc driven T-ALL cell line MOLT4 with increasing doses of Compound 1 at various timepoints. PP2A has been well established to dephosphorylate the c-Myc proto-oncogene via dephosphorylation at Serine62 as a priming event for proteasome-mediated degradation, and prior work in the lab has validated Compound 1 mediates c-Myc proteolysis in in vitro models of c-Myc driven disease.

However, western blot analysis indicates dephosphorylation and subsequent degradation of c-Myc as well as biological affects indicated by Parp cleavage in this cell line precede Y307 dephosphorylation (FIG. 3). These results suggest that the regulation of this tyrosine site is not necessary for the initial activation of PP2A induced by Compound 1, and may be necessary to sustain phosphatase activity and substrate dephosphorylation at longer timepoints.

Figure 4:
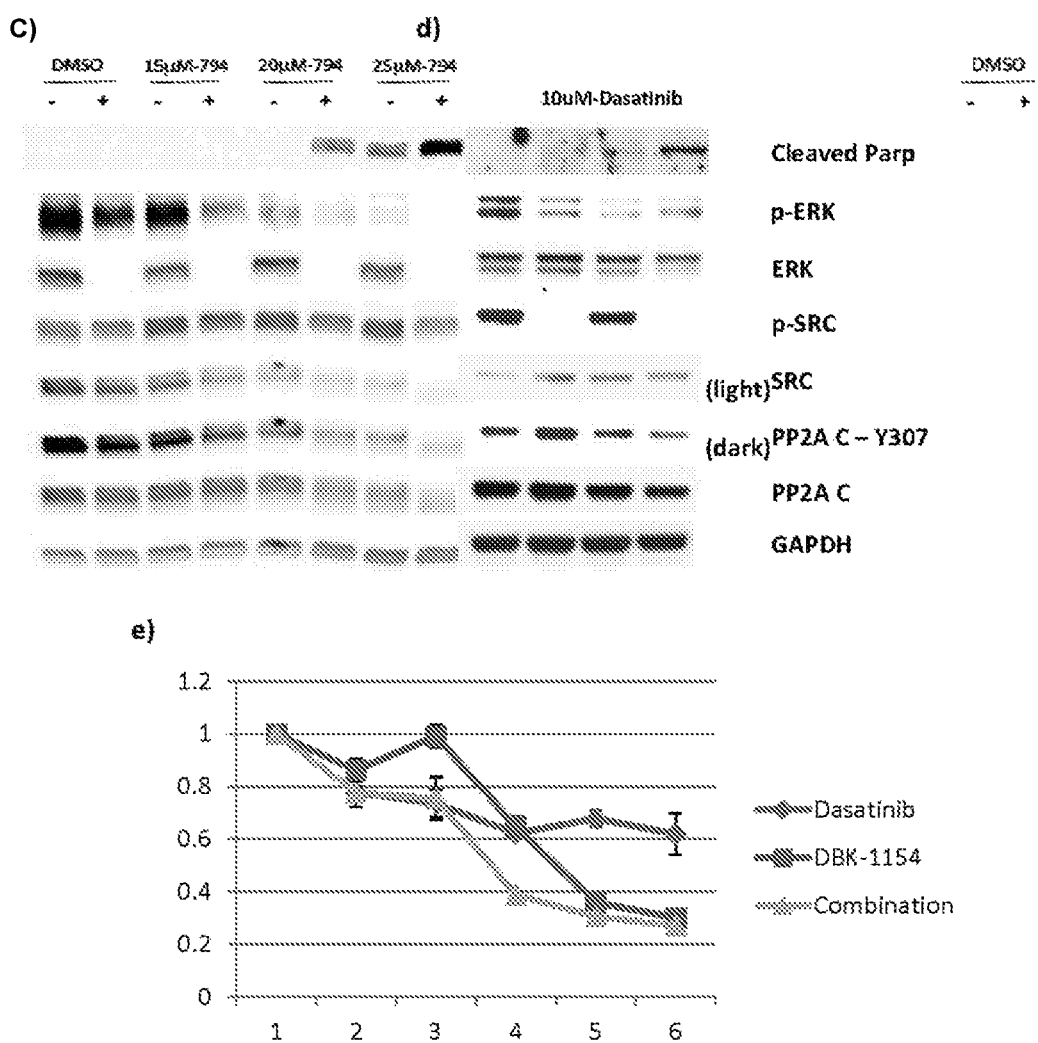
FIGS. 4(A-E) illustrate the effect of dasatinib combinations with SMAPs Compound 1 and Compound 2 in MOLT4 and A549 cell lines. A) Dasatinib addition potentiates the Annexin/PI positivity of MOLT4 cells. B) Dasatinib addition significantly increases the Sub-G1 (apoptotic) fraction in A549 cells by FACS analysis. C) Compound 1 and Dasatinib combination synergistically decrease Y307 phosphorylation in MOLT4, thereby more avidly activating PP2A and dephosphorylating/degrading oncogenic substrates such as c-Myc. D) Dasatinib combination with Compound 2 synergistically activates PP2A by dephosphorylating Y307 with higher affinity in A549. E) MTT assay with Compound 2/Dasatinib dose escalation combinations decreases the $IC_{50}$ of Compound 2 by nearly 2-fold in this cell line.

Compound 1 Displays Increased Biological Activity and Target Engagement when Combined with a SRC Kinase Inhibitor Based upon many prior reports documenting Y307 dephosphorylation as a novel mechanism to activate PP2A and data suggesting Y307 dephosphorylation does not precede PP2A activation in vitro, we hypothesized maximally dephosphorylating this tyrosine site with combinatorial approaches could potentiate the apoptosis induced by Compound 1. Since the proto oncogene SRC has been identified to phosphorylate this site as a means to inactivate PP2A, we combined Compound 1 with Dasatinib, a SRC kinase inhibitor currently FDA-approved to treat Gleevec-resistant CML. These combinatorial approaches significantly potentiated SMAP-induced apoptosis in MOLT4 T-ALL and A549 NSCLC cells, making sub-therapeutic doses of Compound 1 therapeutically active and increasing the activity of already effective doses (FIG. 4A, B). Notably, Dasatinib addition induced significant decreases in Y307 dephosphorylation when combined with SMAPs, leading to increased phosphatase activation and dephosphorylation of the molecular drivers of these cell lines (FIG. 4C, D). Moreover, dose-escalations of both drugs in parallel decreased the GI50 concentration of Compound 2 by nearly two-fold (FIG. 4E). Combined, these results suggest Dasatinib combination with SMAPs can synergistically dephosphorylate Y307, more avidly activate PP2A, and thereby induce increased biological activity in multiple in vitro models of cancer.

Example 2

Methods

Phosphoproteomics Sample Preparation

H358 cells (ATCC) were cultured at 37° C. and 5% $CO_2$ using RPMI media supplemented with 10% FBS and 0.5% penicillin/streptomycin. Per condition, 20 million cells were treated with the appropriate reagent and harvested at the stated time point. The following are the doses used: 17.5 µM DT-061, 1 µM AZD6244, and 0.25 µM MK2206. Cell pellets were then stored at −80° C. for short term. To extract proteins, the cells were pulse sonicated in 2% SDS buffer over ice and in the presence of protease and phosphatase inhibitors. Cysteine amino acid residues were then reduced and alkylated. 800 µg of protein per sample was then digested with Lys-C and Trypsin overnight at 37° C. Subsequent phosphopeptide enrichment was performed using a titanium dioxide column.

Phosphoproteomics Data Processing

The phospho-enriched peptides were analyzed by LC-MS/MS using a LTQ-Orbitrap Velos mass spectrometer (Thermo Scientific, Calif.) equipped with a nanoAcquity™ Ultra-high pressure liquid chromatography system (Waters, Mass.). Separation and detection of peptides were performed using the core's standard procedure. LC-MS/MS raw data were acquired using the x-calibur (Thermo Scientific, 2.2 SP1). The LC-MS/MS raw files were imported and analyzed by the Rosetta Elucidator™ and Mascot programs to sequence the peptides and to identify the parent protein.

Kinase Substrate Enrichment Analysis (KSEA)

The R programming language was used to generate the data and heat maps. The KSEA approach (Casado et al., *Sci Signal.*, 2013) infers a kinase's relative activity output by assessing the collective phosphorylation status of its identified substrates. Kinase-substrate relationships were determined from the PhosphoSitePlus database. For each kinase, the phosphoproteomics dataset was searched for any of the kinase's documented phosphosite substrates. The fold change (FC) for each identified hit was then calculated by taking the median peptide intensity with treatment, divided by median peptide intensity with DMSO. This ratio was then log transformed. To calculate an enrichment score per kinase, all the logged FCs were then averaged and divided by the absolute value of the mean log FC across all phosphosites in the dataset. Consequently, a positive (negative) value represents a kinase with increased (decreased) output upon treatment. This score was then normalized by converting it into a weighted z-score. From there, the statistical enrichment of this score was assessed by determining the probability of having a score more extreme than the actual z-score. All the results were compiled into a heat map for easier visualization. Each kinase score was color coded, for decreased activity output or increased activity output.

Xenograft Studies 5 million cells of H441 and 10 million cells of H358 were injected into the right flank of male BALB/c nu/nu mice (6-8 weeks old). Tumor volume was assessed by caliper measurement. Once the tumors reach about 200 mm$^3$, the mice were randomized to treatment groups, and the study was initiated. The following are the doses per condition: 5 mg/kg of PP2A activator, DT-061, (BID), 25 mg/kg AZD6244 (BID), 25 mg/kg Dasatinib (QD), combination of 24 mg/kg AZD6244 and 6 mg/kg MK2206 (BID), combination of 5 mg/kg DT-061 and 25 mg/kg AZD6244 (BID), and combination of 5 mg/kg DT-061 (BID) and 25 mg/kg Dasatinib (QD). Mice tumor volumes were measured every other day, and body weights were recorded weekly. At the end of the study, the mice were then sacrificed. Blood, liver, and tumor samples were harvested and processed for pharmacodynamics and pharmacokinetics analyses.

Results

Figure 5:
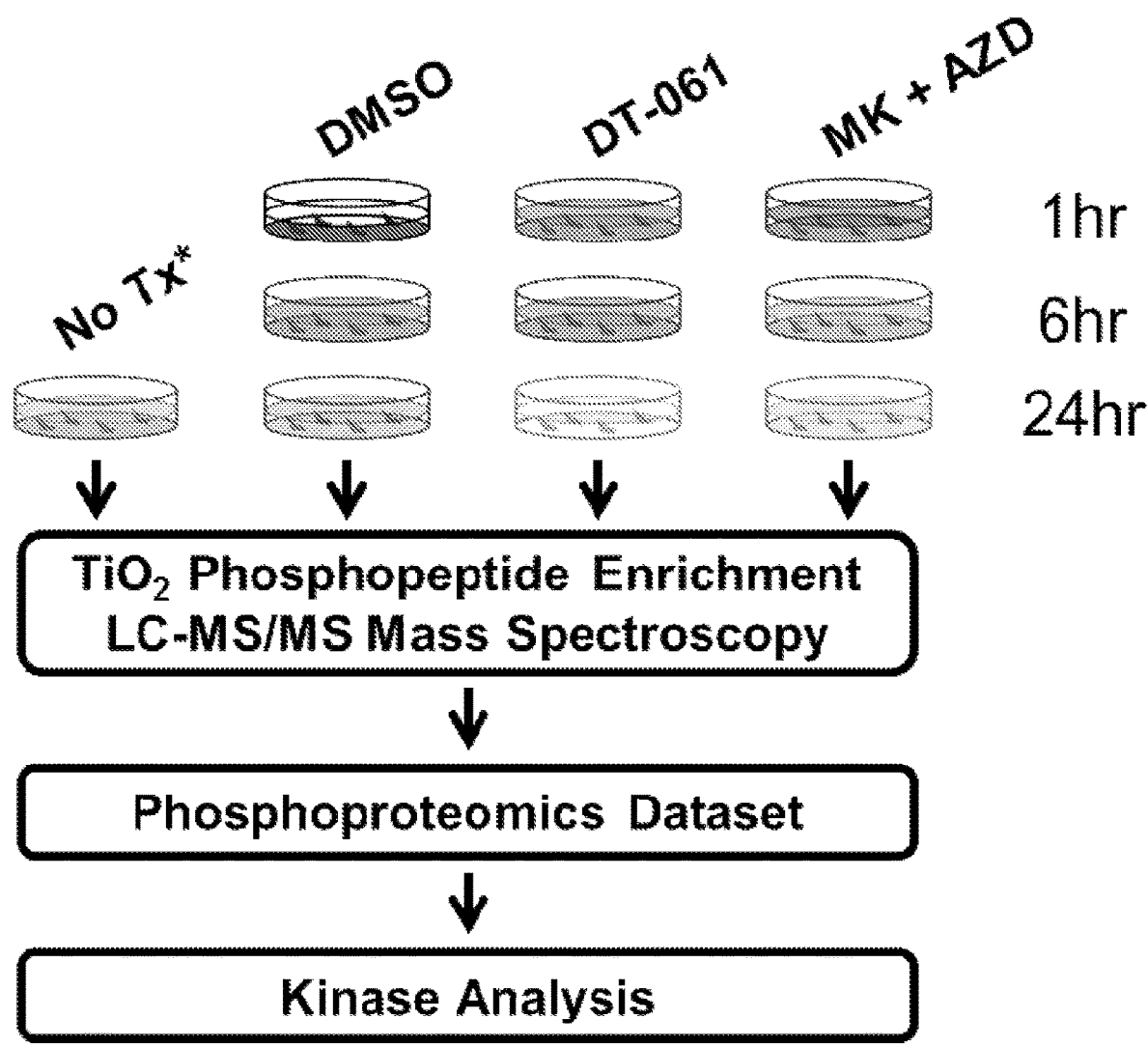
FIG. 5 illustrates an overview of a phosphoproteomics and bioinformatics workflow used to identify anti-cancer drug combinations.

FIG. 5 illustrates an overview of the phosphoproteomics and bioinformatics workflow for leveraging the temporal signaling evolution induced by PP2A activation to design rational anti-cancer drug combination. Each kinase's output was from the collective phosphorylation status of its identified substrates.

Figure 6:
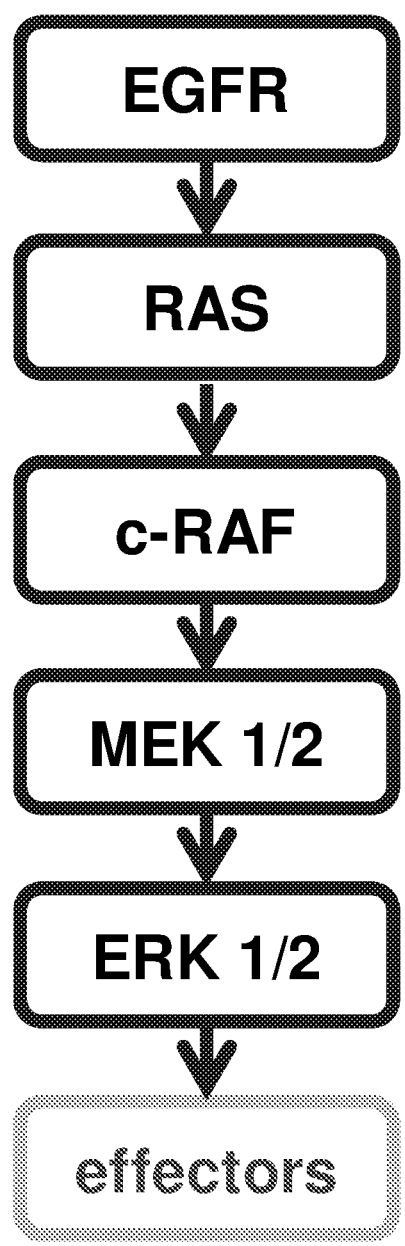
FIG. 6 illustrates canonical signaling for MAPK.
Figure 7:
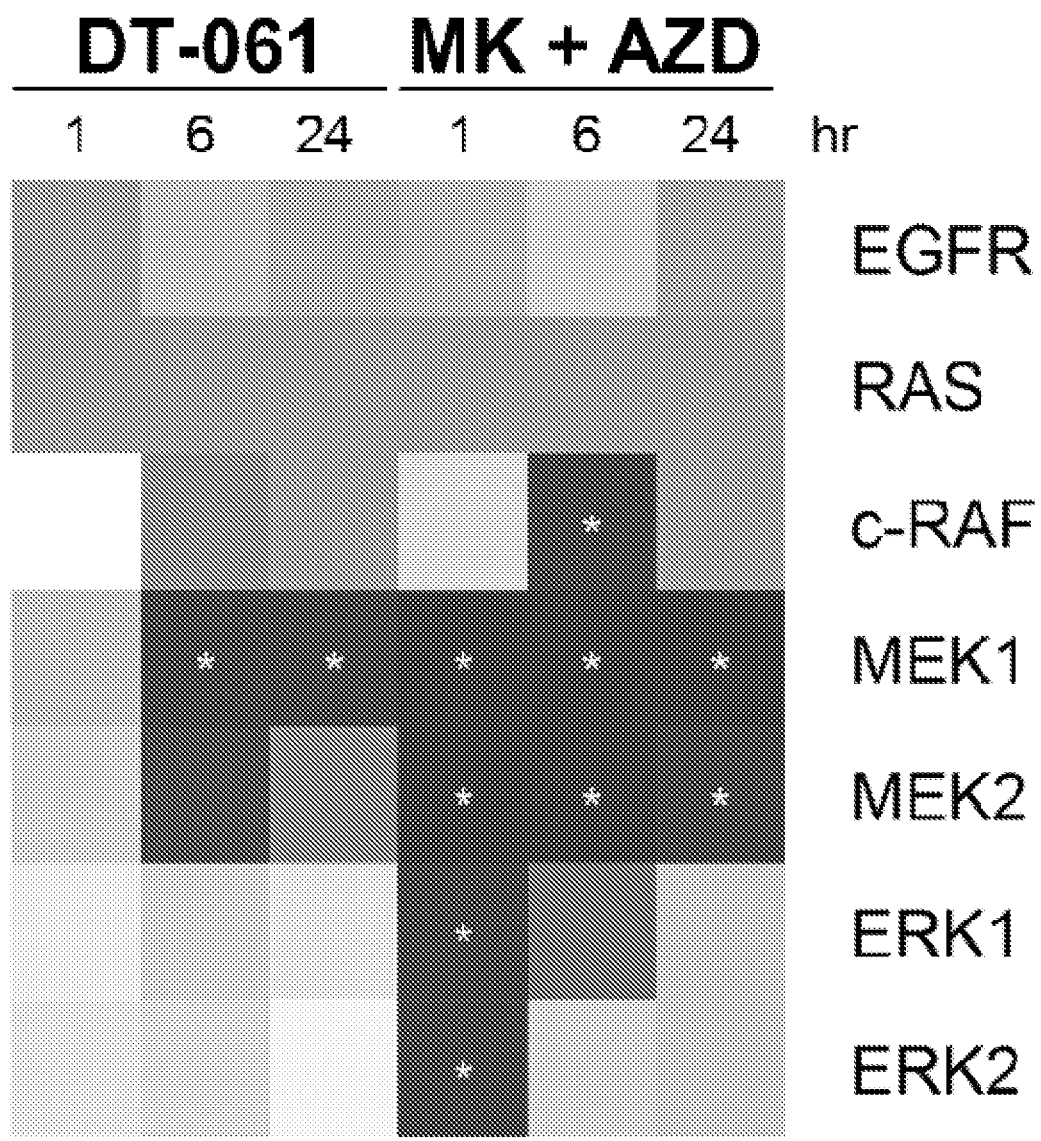
FIG. 7 illustrates KSEA heat map results from the time course phosphoproteomics, showing only kinases pertaining to the canonical MAPK pathway in FIG. 6.

FIG. 7 illustrates KSEA heat map results from the time course phosphoproteomics, showing only kinases pertaining to the canonical MAPK pathway in FIG. 6. KSEA deduces a kinase's activity output based on collective fold change alterations in the phosphorylation state of its known substrates. Blue (red) colors represent kinases with decreased (increased) activity output at the given condition relative to DMSO at the same time-point. Note: EGFR and MEK2 had <4 substrates detected. RAS has no documented phosphorylation substrates and is colored grey. Asterisks mark kinase scores that meet the p<0.05 criterion, adjusted for multiple hypothesis testing. The limited suppression of ERK output with DT-061 suggest that co-treatment with a MEK inhibitor can enhance anti-tumor effects.

Figure 8:
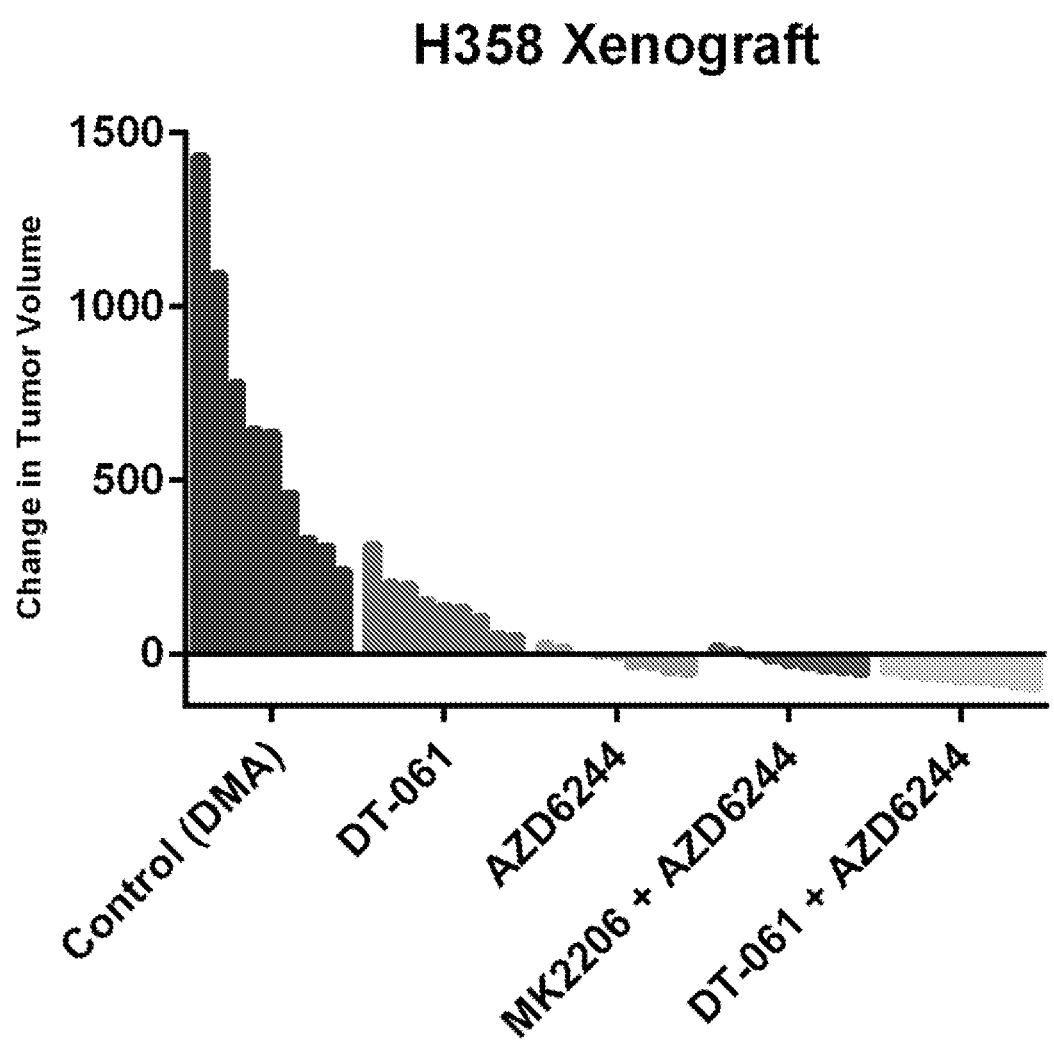
FIG. 8 illustrates waterfall plot of H358 xenograft in NCR Nude mice, showing the difference in tumor volume ($mm^3$) between the start and end of the study across different treatments.

FIG. 8 illustrates waterfall plot of H358 xenograft in NCR Nude mice, showing the difference in tumor volume (mm$^3$) between the start and end of the study across different treatments. Each bar represents an individual tumor. Treatment with AZD6244 plus DT-061 models a vertical pathway inhibition combination.

Figure 9:
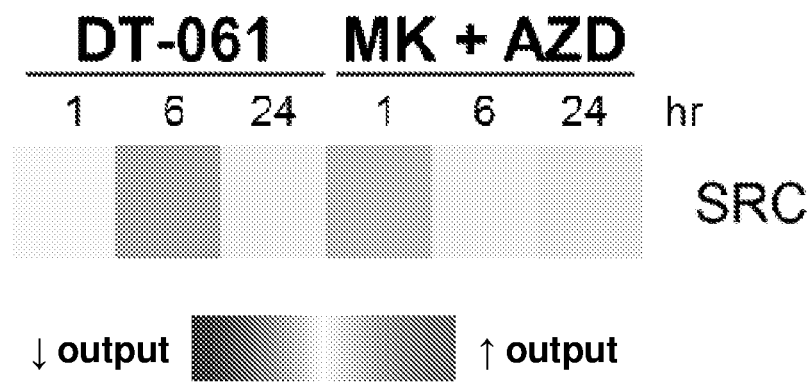
FIG. 9 illustrates KSEA heat map result from the time course phosphoproteomics showing only the output of SRC, a kinase operating separately from the canonical MAPK pathway.

FIG. 9 illustrates KSEA heat map result from the time course phosphoproteomics showing only the output of SRC, a kinase operating separately from the canonical MAPK pathway. Annotation is identical to FIG. 7. The minimal changes in SRC output with DT-061 suggests that co-treatment with a SRC inhibitor can enhance anti-tumor effects.

Figure 10:
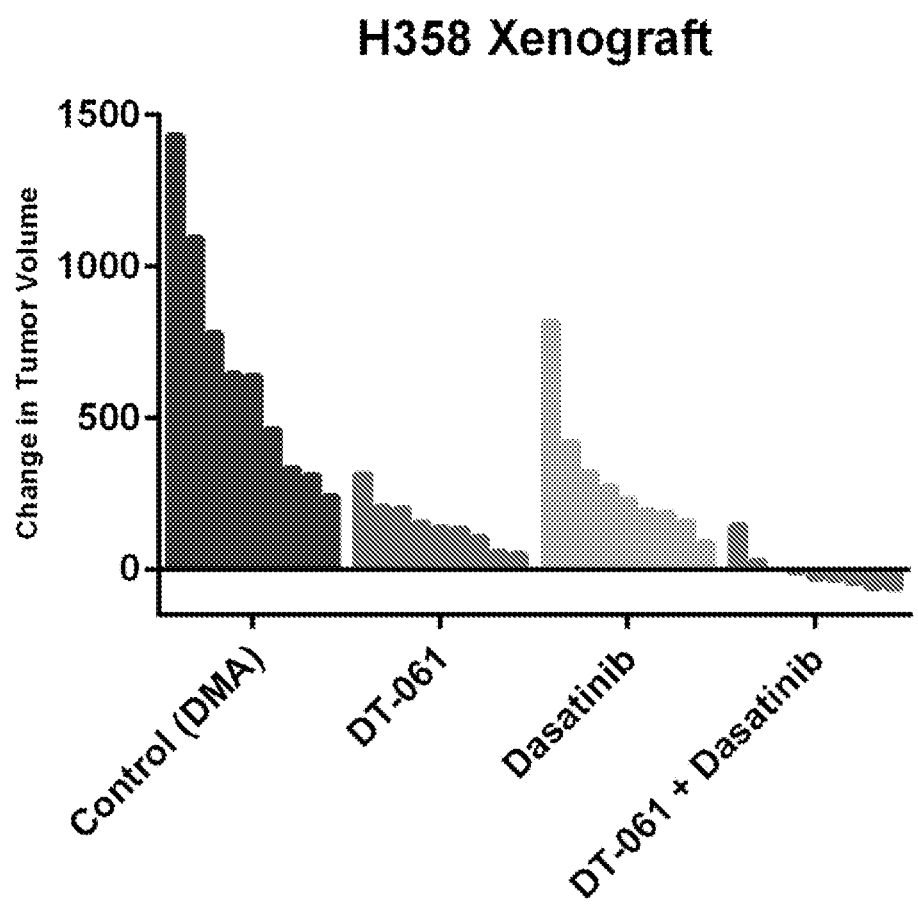
FIG. 10 illustrates a waterfall plot of H358 xenograft tumor volume difference across different treatments.

FIG. 10 illustrates a waterfall plot of H358 xenograft tumor volume difference across different treatments. Same plotting parameters as FIG. 8 apply. Treatment with Dasatinib, a SRC inhibitor, plus DT-061 models a horizontal pathway inhibition combination.

Figure 11:
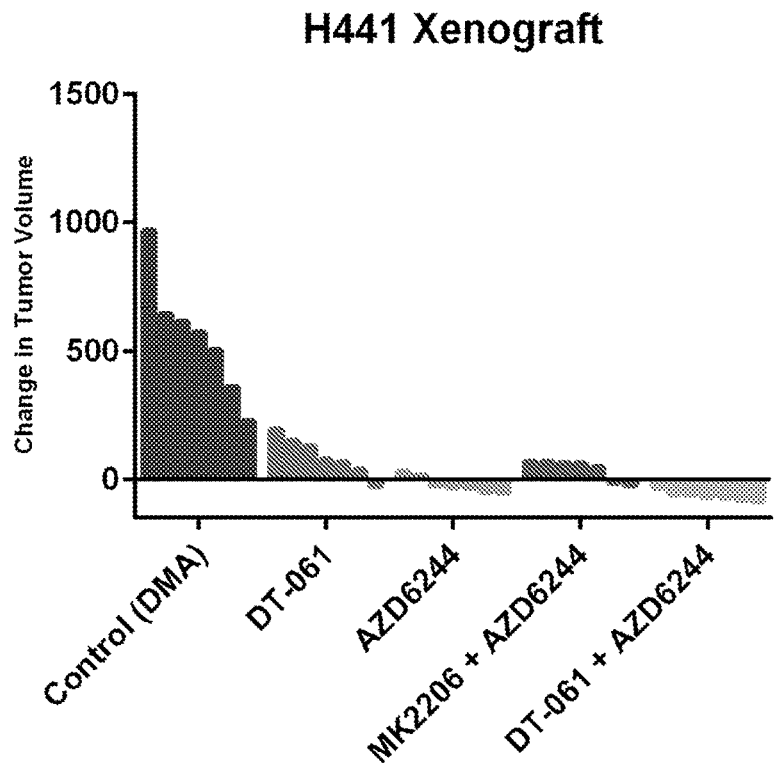
FIG. 11 illustrates a waterfall plot of H441 xenograft tumor volume difference across different treatments.

FIG. 11 illustrates a waterfall plot of H441 xenograft tumor volume difference across different treatments. Treatment with AZD6244 plus DT-061 models a vertical pathway inhibition combination.

Figure 12:
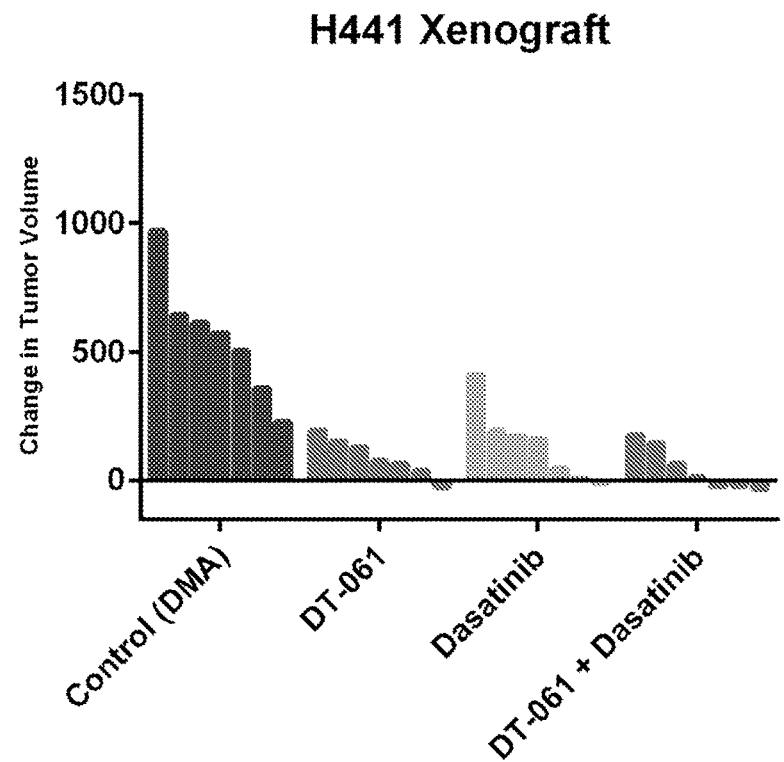
FIG. 12 illustrates a waterfall plot of H441 xenograft tumor volume difference across different treatments.

FIG. 12 illustrates a waterfall plot of H441 xenograft tumor volume difference across different treatments. Treatment with AZD6244 plus DT-061 models a vertical pathway inhibition combination. Same plotting parameters as FIG. 11 apply. Treatment with Dasatinib, a SRC inhibitor, plus DT-061 models a horizontal pathway inhibition combination.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for treating cancer in a subject in need thereof comprising:
   administering to the subject therapeutically effective amounts of a PP2A activator and a protein kinase inhibitor, wherein the cancer is characterized by cancer cells in which PP2A has reduced activity, the PP2A activator comprises a compound of formula (IV):

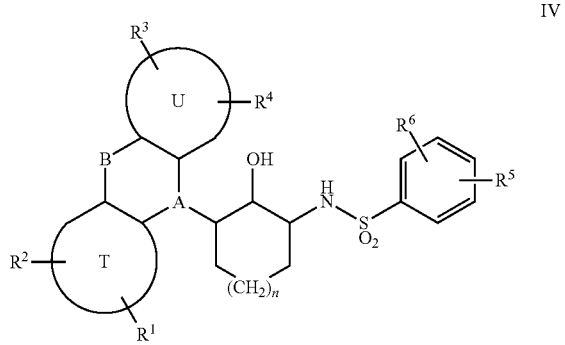

wherein:
B is selected from the group consisting of: direct bond, —O—, (CH$_2$—O), —(O—CH$_2$)—, —C(=O)N(CH$_3$)— and —N(CH$_3$)C(=O)—;
A is selected from N and CH;
T is a benzene ring or a five or six membered heteroaromatic ring;

U is a benzene ring or a five or six membered heteroaromatic ring;

n is zero, 1 or 2;

$R^1$, $R^2$, $R^3$ and $R^4$ are chosen independently from H, OH, halogen, cyano, nitro, $(C_1-C_3)$alkylamino, $(C_1-C_3)$dialkylamino, $(C_1-C_3)$acylamino, $(C_1-C_3)$alkylsulfonyl, $(C_1-C_3)$alkylthio, $(C_1-C_3)$alkyl, $(C_1-C_3)$haloalkyl, $(C_1-C_3)$haloalkoxy, —CC(=O)O$(C_1-C_3)$alkyl, and $(C_1-C_3)$alkoxy;

$R^5$ and $R^6$ are chosen independently from H, halogen, cyano, nitro, azido, $(C_1-C_3)$haloalkyl, $(C_1-C_3)$haloalkoxy, and $(C_1-C_3)$haloalkylthio; and the protein kinase inhibitor inhibits phosphorylation of a catalytic subunit of PP2A; and wherein said cancer is selected from the group consisting of leukemia, prostate, endometrial and non-small cell lung cancer.

2. The method of claim 1, wherein the subject is administered a pharmaceutical composition including a coformulation of the PP2A activator and the protein kinase inhibitor.

3. The method of claim 1, wherein the PP2A activator is a tricyclic neuroleptic compound devoid of GPCR or monoamine transporter pharmacology.

4. The method of claim 1, wherein the amount of protein kinase inhibitor is subtherapeutic when administered in the absence of the PP2A activator.

5. The method of claim 1, wherein the protein kinase inhibitor is selected from an MEK-1 inhibitor, EGFR inhibitor, Her-2 kinase inhibitor, Src inhibitor, IKK inhibitor, Jak2 inhibitor, Aurora kinase inhibitor, CHK1 inhibitor, and a GSK-3 inhibitor.

6. The method of claim 5, wherein the protein kinase inhibitor is selected from the group consisting of trametinib, selumetinib, and cobimetinib.

7. The method of claim 5, wherein the protein kinase inhibitor is an EGFR inhibitor selected from erlotinib, gefitinib, lapatinib, and icotinib.

8. The method of claim 5, wherein the protein kinase inhibitor is a Src inhibitor selected from the group consisting of sarcatinib, dasatinib and bosutinib.

9. The method of claim 5, wherein the protein kinase inhibitor is an IKK inhibitor selected from the group consisting of N-(6-chloro-9H-pyrido[3,4-b]indol-8-yl)nicotinamide, $N^1$-(1,8-dimethylimidazo[1,2-a]quinoxalin-4-yl)ethane-1,2-diamine, 1-((5-methoxy-2-(thiophen-2-yl)quinazolin-4-yl)amino)-3-methyl-1H-pyrrole-2,5-dione, N-(6-chloro-7-methoxy-9H-pyrido[3,4-b]indol-8-yl)-2-methylnicotinamide, 4-amino-[2,3'-bithiophene]-5-carboxamide; (E)-1-(6-(4-chlorophenoxy)hexyl)-2-cyano-3-(pyridin-4-yl)guanidine, and (Z)-3-(2,4-dimethyl-5-((2-oxoindolin-3-ylidene)methyl)-1H-pyrrol-3-yl)propanoic acid.

10. The method of claim 5, wherein the protein kinase inhibitor is the Jak2 inhibitor ruxolitinib, Baricitinib, CYT387, lestaurtinib, pacritinib and TG101348.

11. The method of claim 5, wherein the protein kinase inhibitor is a Aurora kinase inhibitor selected from the group consisting of ZM447439, VX-680 (MK-0457), Hesperadin, PHA-680632, PHA-739358, Compound 677, JNJ-7706621, MLN8054, MLN8237, AZD1152, AS703569, PF-03814735, and SNS-314.

12. The method of claim 5, wherein the protein kinase inhibitor is a CHK1 inhibitor selected from the group consisting of (S)-5-(3-fluorophenyl)-N-(piperidin-3-yl)-3-ureidothiophene-2-carboxamide, (S)-1-(5-bromo-4-methyl-2-(morpholin-2-ylmethoxy)phenyl)-3-(5-methylpyrazin-2-yl)urea (Rabusertib), 6-bromo-3-(1-methyl-1H-pyrazol-4-yl)-5-(piperidin-3-yl)pyrazolo[1,5-a]pyrimidin-7-amine, (S)-3-(1H-benzo[d]imidazol-2-yl)-6-chloro-4-(quinuclidin-3-ylamino)quinolin-2(1H)-one, and (R)-2-amino-2-cyclohexyl-N-(5-(1-methyl-1H-pyrazol-4-yl)-1-oxo-2,6-dihydro-1H-[1,2]diazepino[4,5,6-cd]indol-8-yl)acetamide.

13. The method of claim 5, wherein the protein kinase inhibitor is a GSK-3 inhibitor selected from the group consisting of 3-((3-chloro-4-hydroxyphenyl)amino)-4-(2-nitrophenyl)-1H-pyrrole-2,5-dione, dichlorophenyl)-4-(1-methyl-1H-indol-3-yl)-1H-pyrrole-2,5-dione, 6-((2-((4-(2,4-dichlorophenyl)-5-(4-methyl-1H-imidazol-2-yl)pyrimidin-2-yl)amino)ethyl)amino)nicotinonitrile, $N^2$-(2-((4-(2,4-dichlorophenyl)-5-(1H-imidazol-2-yl)pyrimidin-2-yl)amino)ethyl)-5-nitropyridine-2,6-diamine, 1-(quinolin-4-yl)-3-(6-(trifluoromethyl)pyridin-2-yl)urea, 4-benzyl-2-(naphthalen-1-yl)-1,2,4-thiadiazolidine-3,5-dione, and 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione.

14. The method of claim 1, wherein the PP2A activator is selected from the group consisting of:

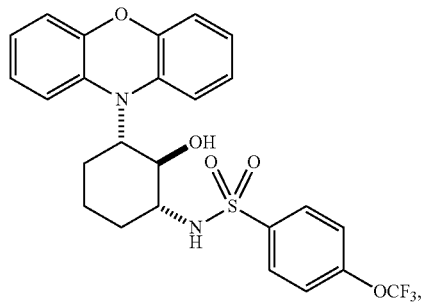

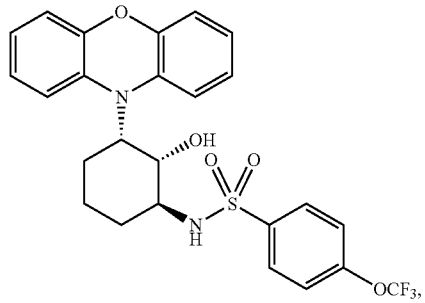

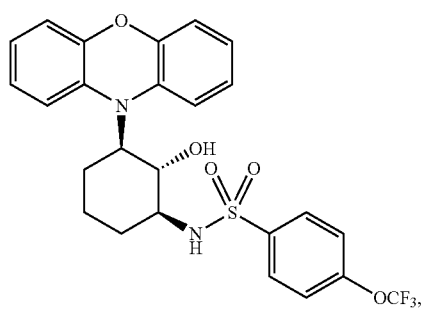

51
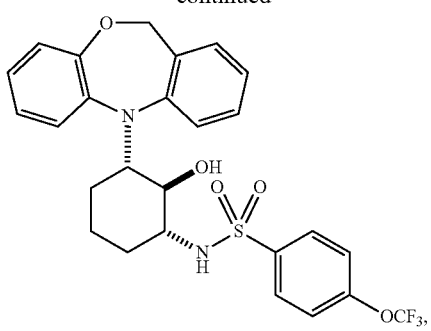
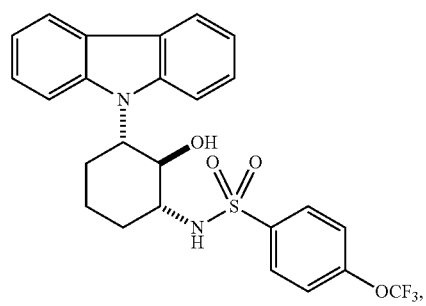
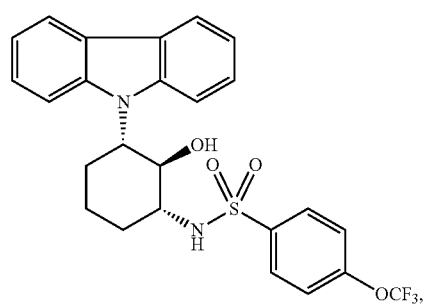
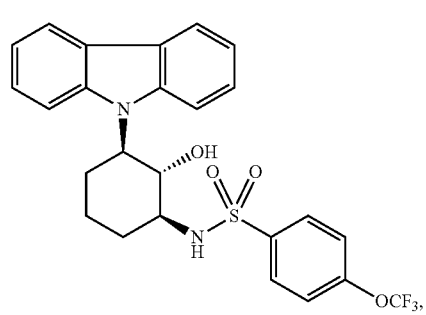
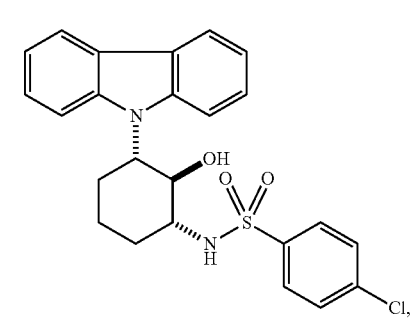
52
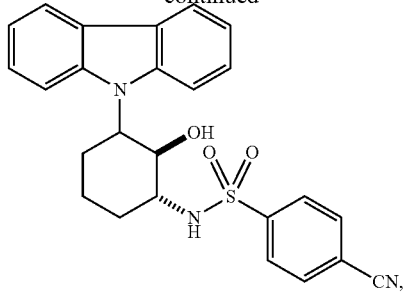
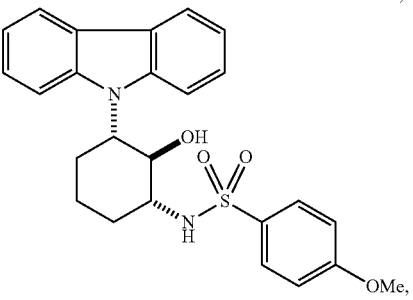
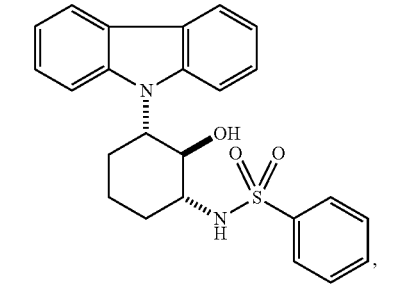
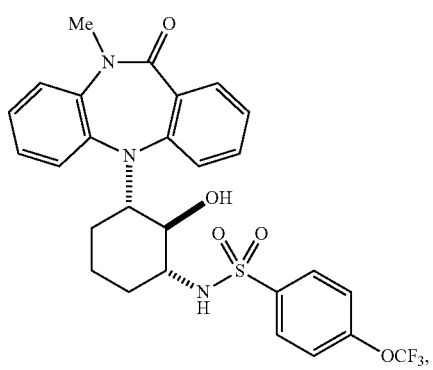
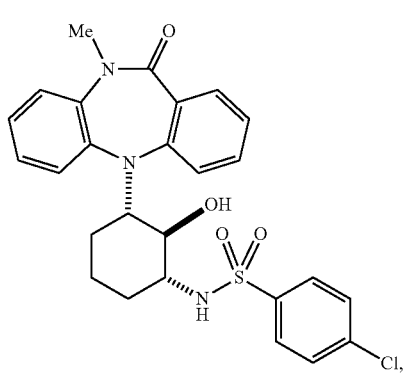

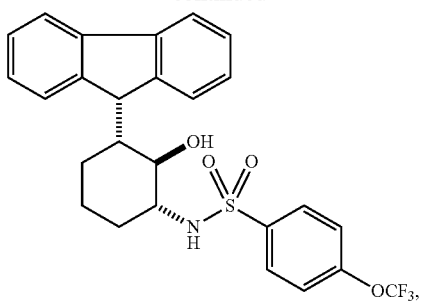
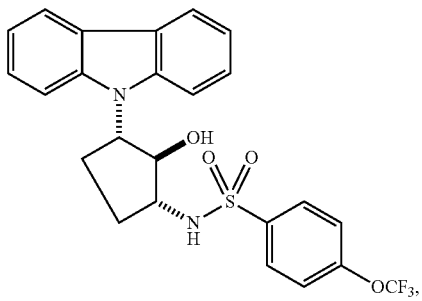
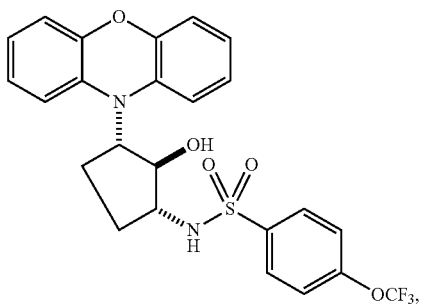
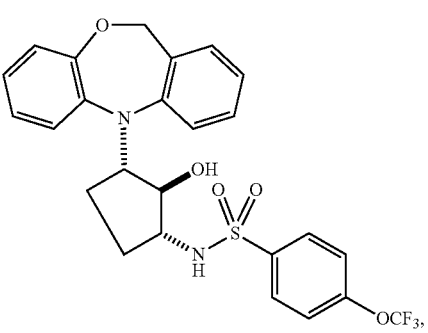
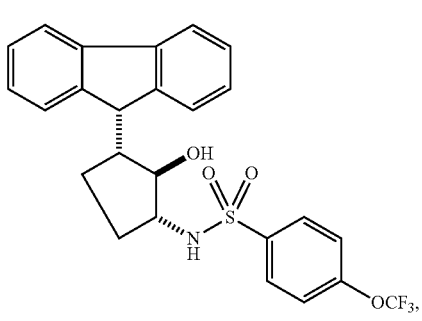
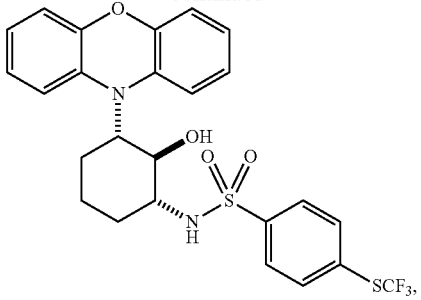
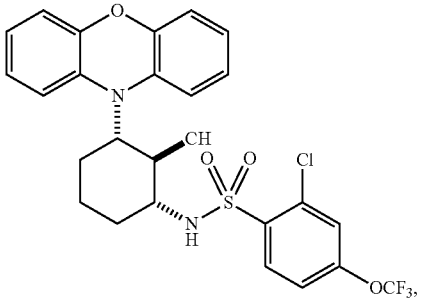
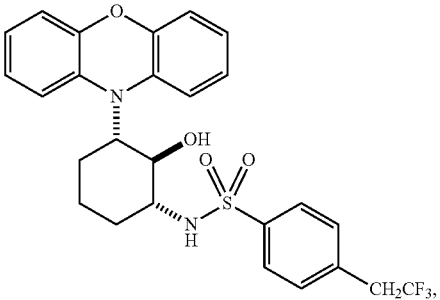
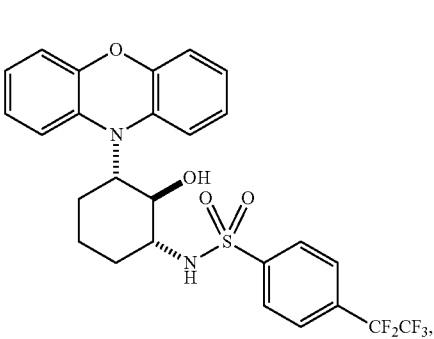
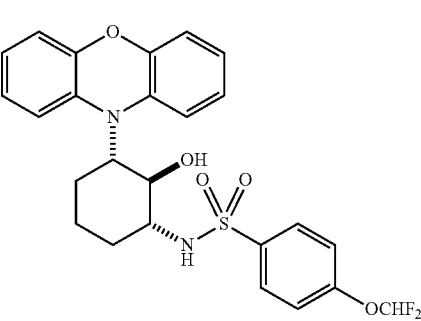

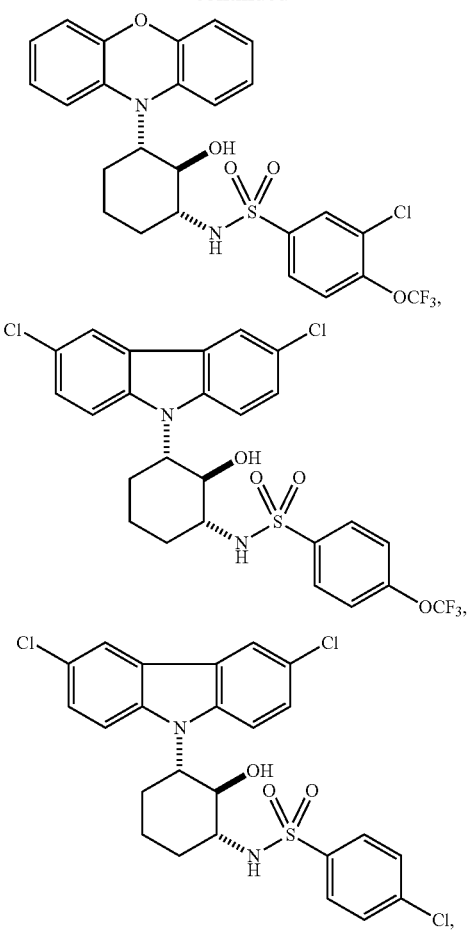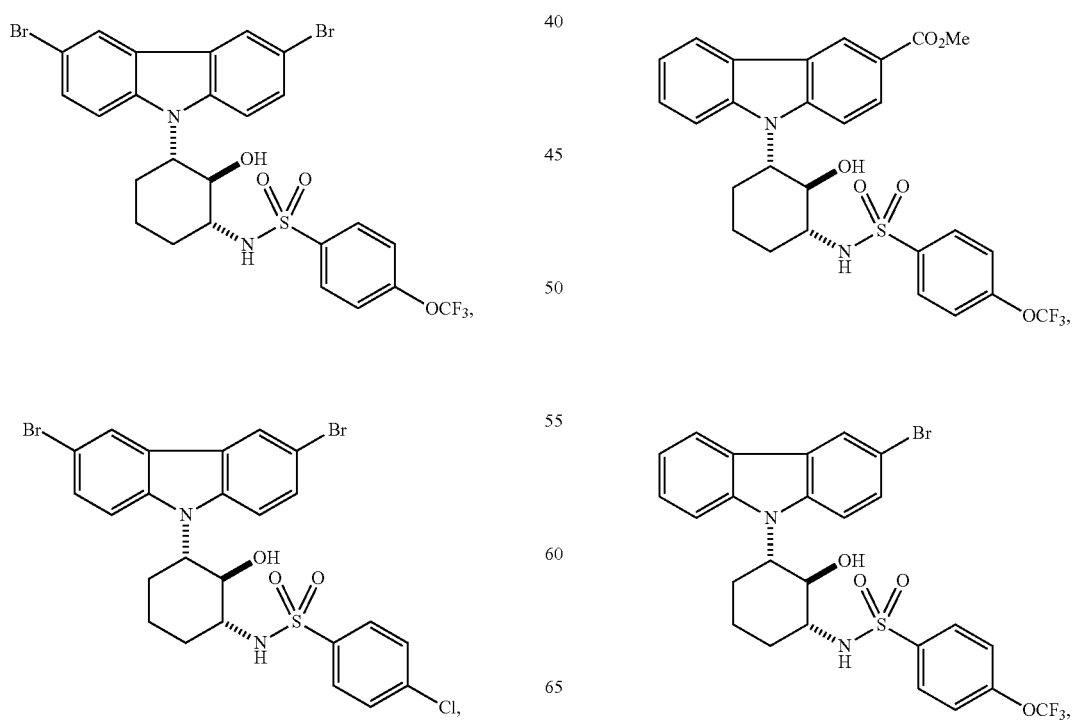

57
-continued
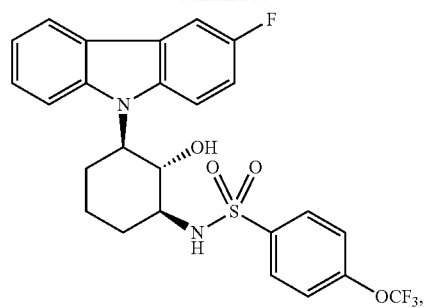
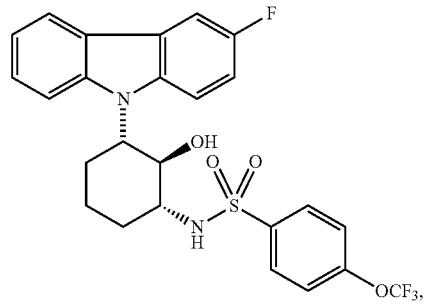
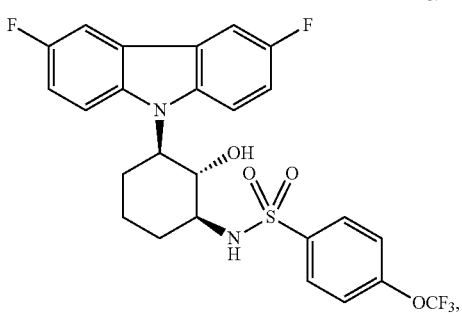
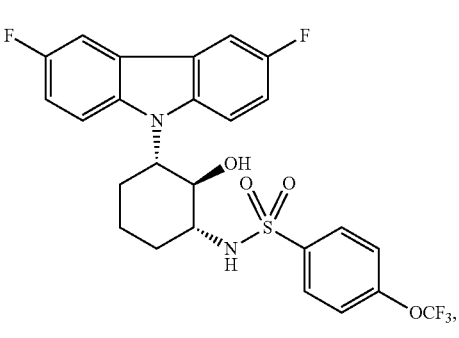
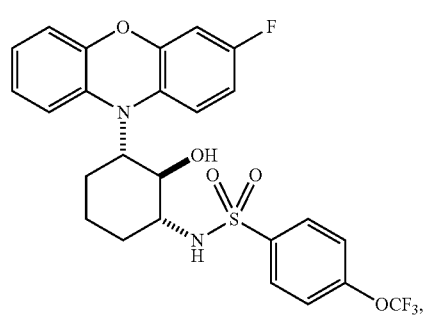
58
-continued
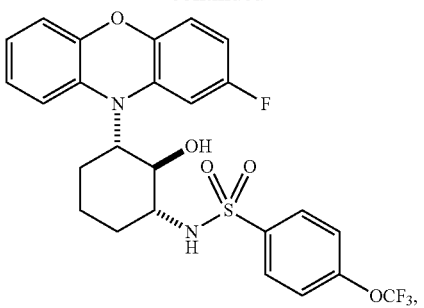
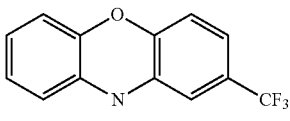
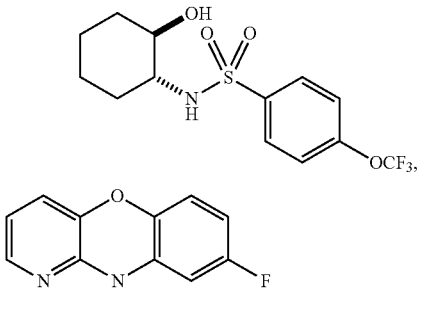
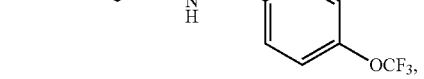
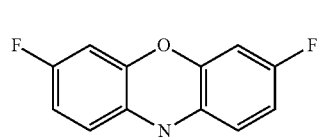
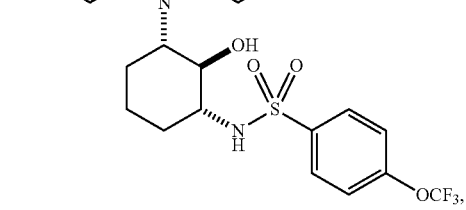
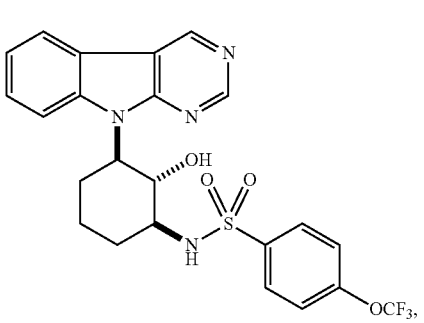

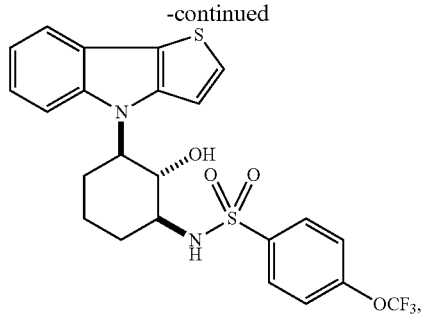
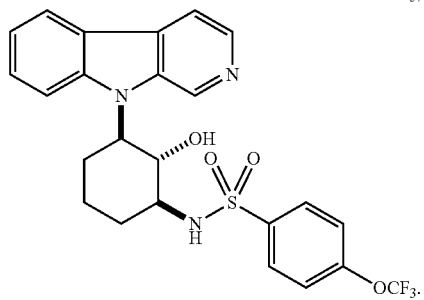
* * * * *